United States Patent
Ludlow et al.

(10) Patent No.: US 7,606,623 B2
(45) Date of Patent: Oct. 20, 2009

(54) METHODS AND DEVICES FOR INTRAMUSCULAR STIMULATION OF UPPER AIRWAY AND SWALLOWING MUSCLE GROUPS

(75) Inventors: Christy L. Ludlow, Bethesda, MD (US); Eric Mann, Clarksville, MD (US); Theresa Burnett, Bloomington, IN (US); Steven Bielamowicz, McLean, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 417 days.

(21) Appl. No.: 10/529,401

(22) PCT Filed: Sep. 26, 2003

(86) PCT No.: PCT/US03/30032

§ 371 (c)(1),
(2), (4) Date: Jan. 4, 2006

(87) PCT Pub. No.: WO2004/028433

PCT Pub. Date: Apr. 8, 2004

(65) Prior Publication Data

US 2007/0123950 A1 May 31, 2007

Related U.S. Application Data

(60) Provisional application No. 60/413,773, filed on Sep. 27, 2002.

(51) Int. Cl.
*A61N 1/00* (2006.01)
(52) U.S. Cl. .......................................... 607/62; 607/63
(58) Field of Classification Search .................. 607/42, 607/72, 62, 63, 59
See application file for complete search history.

(56) References Cited

U.S. PATENT DOCUMENTS 5,111,814 A 5/1992 Goldfarb (Continued)

FOREIGN PATENT DOCUMENTS

WO WO 92/21407 12/1992

(Continued)

OTHER PUBLICATIONS

Supplementary European Search Report dated May 14, 2008.

(Continued)

*Primary Examiner*—Scott M Getzow
(74) *Attorney, Agent, or Firm*—Merchant & Gould P.C.

(57) ABSTRACT

Devices and methods were discovered that successfully provided patient autonomous control of both hyolaryngeal elevation, anterior hyoid motion and opening of the upper esophageal sphincter for swallowing by intramuscular stimulation of two muscles. The technology allows patient self stimulation of swallowing and can return oral feeding to dysphagia patients. Indwelling electrode stimulation of only two muscles generated as much as 80 % of normal synergistic movement leading to swallowing. The devices and methods also are useful for control of other upper respiratory muscle groups involved in speech and voice. Calibration techniques may be used in combination for greater freedom in setting and using electrodes over extended implantation time periods. These methods and devices can control complex movements of body solids such as bone and cartilage and tissues by electro stimulation of a minimum set of muscles simultaneously.

34 Claims, 9 Drawing Sheets

U.S. PATENT DOCUMENTS

| | | | |
|---|---|---|---|
| 5,725,564 | A | 3/1998 | Freed et al. |
| 5,871,508 | A | 2/1999 | Thompson et al. |
| 5,891,185 | A * | 4/1999 | Freed et al. .................. 607/72 |
| 5,897,579 | A * | 4/1999 | Sanders ........................ 607/42 |
| 6,104,958 | A | 8/2000 | Freed et al. |
| 6,198,970 | B1 | 3/2001 | Freed et al. |
| 6,343,232 | B1 | 1/2002 | Mower |
| 6,354,991 | B1 | 3/2002 | Gross et al. |
| 6,393,323 | B1 | 5/2002 | Sawan et al. |
| 2002/0010495 | A1 | 1/2002 | Freed et al. |
| 2002/0049479 | A1 | 4/2002 | Pitts |
| 2002/0133194 | A1 | 9/2002 | Leelamanit et al. |

FOREIGN PATENT DOCUMENTS

| | | |
|---|---|---|
| WO | WO 97/15349 | 5/1997 |
| WO | WO 2004/028433 A2 | 4/2004 |
| WO | WO 2007/005582 | 1/2007 |

OTHER PUBLICATIONS

Humbert et al., "The effect of surface electrical stimulation on hyolaryngeal movement in normal individuals at rest and during swallowing", *J Appl Physiol*, 101:1657-1663 (2006).

Humbert et al., "The Effect of Surface Electrical Stimulation on Vocal Fold Position", *Laryngoscope*, 118:14-19 (2007).

Ludlow et al., "Effects of Surface Electrical Stimulation Both at Rest and During Swallowing in Chronic Pharyngeal Dysphagia", *Dysphagia*, 22:1-10 (2007).

Aviv et al., "Laryngopharyngeal sensory testing with modified barium swallow as predictors of aspiration pneumonia after stroke", *Laryngoscope*, 107:1254-1260 (1997).

Aviv et al., "Silent laryngopharyngeal sensory deficits after stroke", *Ann Otol Rhinol. Laryngol.*, 106:87-93 (1997).

Aviv et al., "Supraglottic and pharyngeal sensory abnormalities in stroke patients with dysphagia", *Ann Otol Rhinol.Laryngol.*, 105:92-97 (1996).

Bara-Jimenez et al., "Abnormal somatosensory homunculus in dystonia of the hand", *Ann Neurol.*, 44(5):828-831 (1998).

Bara-Jimenez et al., "Sensory discrimination capabilities in patients with focal hand dystonia", *Ann Neurol.*, 47(3):377-380 (2000).

Bielamowicz et al., "Effects of botulinum toxin on pathophysiology in spasmodic dysphonia", *Ann Otol Rhinol Laryngol*, 109:194-203 (2000).

Burnett et al., "Self-Triggered Functional Electrical Stimulation During Swallowing", *J Neurophysiol*, 94(6):4011-4018 (2005).

Conforto et al. "Increase in hand muscle strength of stroke patients after somatosensory stimulation", *Ann Neurol*, 51(1):122-125 (2002).

de Larminat et al., "Alteration in swallowing reflex after extubation in intensive care unit patients", *Crit Care Med*, 23(3):486-490 (1995).

De Nil et al., "Kinaesthetic acuity of stutterers and non-stutterers for oral and non-oral movements", *Brain*, 114:2145-2158 (1991).

Dick et al., "Interaction between central pattern generators for breathing and swallowing in the cat", *J Physiol*, 465:715-730 (1993).

Folstein et al., "Mini-mental state. A practical method for grading the cognitive state of patients for the clinician", *J Psychiatr Res*, 12(3):189-198 (1975).

Fraser et al., "Differential changes in human pharyngoesophageal motor excitability induced by swallowing, pharyngeal stimulation, and anesthesia", *Am J Physiol Gastrointest Liver Physiol*, 285(1):G137-144 (2003).

Hägg et al., "Effects of motor and sensory stimulation in stroke patients with long-lasting dysphagia", *Dysphagia*, 19:219-230 (2004).

Hamdy et al., "Modulation of human swallowing behaviour by thermal and chemical stimulation in health and after brain injury", *Neurogastroenterol Motil*, 15(1):69-77 (2003).

Haslinger et al., "Silent event-related fMRI reveals reduced sensorimotor activation in laryngeal dystonia", *Neurology*, 65:1562-1569 (2005).

Jafari et al., "Sensory regulation of swallowing and airway protection: a role for the internal superior laryngeal nerve in humans", *J Physiol*, 550(Pt I):287-304 (2003).

Jean, "Control of the central swallowing program by inputs from the peripheral receptors. A review", *J Auton. Ner. Syst.*, 10:225-233 (1984).

Leelamanit et al., "Synchronized electrical stimulation in treating pharyngeal dysphagia", *Laryngoscope*, 112(12):2204-2210 (2002).

Logemann et al., "Effects of a sour bolus on oropharyngeal swallowing measures in patients with neurogenic dysphagia", *J Speech Hear Res*, 38(3):556-563 (1995).

Logemann, "Noninvasive approaches to deglutitive aspiration", *Dysphagia*, 8(4):331-333 (1993).

Loucks et al., "Laryngeal muscle responses to mechanical displacement of the thyroid cartilage in humans", *J Appl Physiol*, 99(3):922-930 (2005).

Lowell et al., "Sensory stimulation activates both motor and sensory components of the swallowing system", *NeuroImage*, 42:285-295 (2008).

Ludlow et al., "Dynamic aspects of phonatory control in spasmodic dysphonia", *J Speech Hear Res*, 30:197-206 (1987).

Mifflin, "Intensity and frequency dependence of laryngeal afferent inputs to respiratory hypoglossal motoneurons", *J Appl Physiol*, 83:1890-1899 (1997).

Nishino et al. (1996). Cough and other reflexes on irritation of airway mucosa in man. Pulm Pharmacol, 9(5-6):285-292 (1996).

Ootani et al., "Convergence of afferents from the SLN and GPN in cat medullary swallowing neurons", *Brain Res Bull*, 37(4):397-404 (1995).

Park et al., "A pilot exploratory study of oral electrical stimulation on swallow function following stroke: an innovative technique", *Dysphagia*, 12(3):161-166 (1997).

Peurala et al., "Cutaneous electrical stimulation may enhance sensorimotor recovery in chronic stroke", *Clin Rehabil.*, 16:709-716 (2002).

Pick et al., "Pulmonary aspiration in a long-term care setting: clinical and laboratory observations and an analysis of risk factors", *J Am Geriatr Soc*, 44(7):763-768 (1996).

Pommerenke, "A study of the sensory areas eliciting the swallowing reflex", *American Journal of Physiology*, 84(1):36-41 (1927).

Portone et al., "A review of patient adherence to the recommendations for voice therapy", *J. Voice*, 22:192-196 (2008).

Power et al., "Changes in pharyngeal corticobulbar excitability and swallowing behavior after oral stimulation", *Am J Physiol Gastrointest Liver Physiol*, 286(1):G45-50 (2004).

Power et al., "Evaluating oral stimulation as a treatment for Dysphagia after stroke", *Dysphagia*, 21(1):49-55 (2006).

Robbins et al., "Swallowing and dysphagia rehabilitation: translating principles of neural plasticity into clinically orientated evidence", *J Speech Lang. Hear. Res.*, 51:S276-300 (2008).

Sedory-Holzer et al., "The swallowing side effects of botulinum toxin type A injection in spasmodic dysphonia", *Laryngoscope*, 106:86-92 (1996).

Setzen et al., "The association between laryngopharyngeal sensory deficits, pharyngeal motor function, and the prevalence of aspiration with thin liquids", *Otolaryngol Head Neck Surg*, 128(1):99-102 (2003).

Struppler et al., "Modulation of sensorimotor performances and cognition abilities induced by RPMS: clinical and experimental investigations", *Suppl Clin Neurophysiol.*, 56:358-367 (2003).

Theurer et al., "Oropharyngeal stimulation with air-pulse trains increases swallowing frequency in healthy adults", *Dysphagia*, 20(4):254-260 (2005).

van Dijk et al., "Effects of transcutaneous electrical nerve stimulation (TENS) on non-pain related cognitive and behavioural functioning", *Rev Neurosci.*, 13:257-270 (2002).

Bidus et al., "Effects of Adductor Muscle Stimulation on Speech in Abductor Spasmodic Cysphonia", *The Laryngoscope*, 110:1943-1949 (2000).

Burnett et al., "Laryngeal elevation achieved by neuromuscular stimulation at rest", *J. Appl. Physiol.*, 94:128-134 (2003).

Daly et al., "Performance of an intramuscular electrode during functional neuromuscular stimulation for gait training post stroke", *Journal of Rehabilitation Research and Development*, 38(5):513-526 (2001).

Freed et al., "Electrical Stimulation for Swallowing Disorders Caused by Stroke", *Respiratory Care*, 46(5):466-474 (2001).

Handa et al., "Development of Percutaneous Intramuscular Electrode for Multichannel FES System", *IEEE Transactions on Biomedical Engineering*, 36(7):705-710, Jul. 1989.

Hrycyshyn et al., "Electromyography of the Oral Stage of Swallowing in Man", *Am. J. Anat.*, 133:333-340 (1972).

Ludlow et al., "Three-Dimensional Changes in the Upper Airway During Neuromuscular Stimulation of Laryngeal Muscles", *Journal of Artificial Organs*, 23:463-465 (1999).

Ludlow et al., "Chronic Intermittent Stimulation of the Thyroarytenoid Muscle Maintains Dynamic Control of Glottal Adduction", *Muscle and Nerve*, 23:44-57 (2000).

Lundy et al., "Aspiration: Cause and Implications", *Otolaryngol Head Neck Surg.*, 120:474-478 (1999).

Marsolais et al., "Implantation techniques and experience with percutaneous intramuscular electrodes in the lower extremities", *J. Rehabil. Res. Dev.*, 23(3):1-8 (1986).

Mortimer et al., "Intramuscular Electrical Stimulation: Tissue Damage", *Ann. Biomed. Eng.*, 8:235-244 (1980).

Scheiner et al., "Design and Clinical Application of a Double Helix Electrode for Functional Electrical Stimulation", *IEEE Transactions of Biomedical Engineering*, 41(5):425-431 (1994).

Spiro et al., "Activation and Coordination Patterns of the Suprahyoid Muscles During Swallowing", *Laryngoscope*, 104:1376-1382 (1994).

Stanic et al., "Multichannel Electrical Stimulation for Correction of Hemiplegic Gait", *Scand J. Rehabil. Med.*, 10:75-92 (1978).

Strojnik et al., "Treatment of Drop Foot Using an Implantable Peroneal Underknee Stimulator", *Scand J. Rehabil. Med.*, 19:37-43 (1987).

Sundgren et al., "Elevation of the larynx on normal and abnormal cineradiogram", *The British Journal of Radiology*, 66:768-772 (1993).

Waters et al., "Functional Electrical Stimulation of the Peroneal Nerve for Hemiplegia", *The Journal of Bone and Joint Surgery*, 67:792-793 (1985).

International Search Report dated Apr. 9, 2004 (PCT/US03/30032).

International Search Report dated Nov. 21, 2006 (PCT/US2006/025535).

* cited by examiner

METHODS AND DEVICES FOR INTRAMUSCULAR STIMULATION OF UPPER AIRWAY AND SWALLOWING MUSCLE GROUPS

This application is a 371 of PCT/US2003/030032 filed on Sep. 26, 2003, which is hereby incorporated by reference.

This application claims priority to U.S. provisional application 60/413,773 filed Sep. 27, 2002, the entirety of which is hereby incorporated by reference.

STATEMENT OF RIGHTS TO INVENTION MADE UNDER FEDERALLY SPONSORED RESEARCH AND DEVELOPMENT

The work performed during the development of this application utilized support from the National Institutes of Health. The U.S. government has certain rights in the invention.

FIELD OF THE INVENTION

The invention relates generally to devices and procedures for modifying muscular function and more specifically to control of muscular activity by electrode stimulation.

BACKGROUND OF THE INVENTION

Dysphagia is a common complication with diseases such as stroke, neurodegenerative diseases, brain tumors, respiratory disorders, and the like wherein insufficient control of muscles needed for swallowing engender a risk of aspiration pneumonia. Aspiration pneumonia has been estimated to inflict a 20% death rate in the first year after a stroke and 10-15% each year thereafter. Treatment for this disorder requires either feeding through a nasogastric tube on a temporary basis or enteric feeding through a stoma to the stomach in chronically affected cases. The treatment costs and the commensurate value of a remediation technology if one were available, are very high. For example, in 1992 Medicare paid for enteral feedings of 206,000 patients at a cost of $505 million in one year. Furthermore, this cost is an underestimate because Medicare pays only half of the enteric home feeding costs and approximately 412,000 patients per year receive enteric feedings due to risk of aspiration in the United States alone. Accordingly, any technology that can significantly reduce the number of patients who require this extra care due to insufficient control of muscles used for swallowing would provide great monetary and quality of life benefits to the nation.

Dysphagia often results from poor control of some muscles in the upper respiratory system. Many muscles in this system affect important complex movements during speech and voice. Patients sometimes lack proper control of muscles used for these other activities and unfortunately remedial efforts leave much to be desired here as well. Electrical stimulation of upper respiratory system muscles has been used to alleviate pain and to stimulate nerves, as well as to treat disorders of the spinal cord or peripheral nervous system. Stimulation further has been used to facilitate upper respiratory muscle reeducation and in conjunction with other physical therapy treatments.

Generally the technique of stimulating muscles in the body has been used to induce contraction of individual muscles in other systems. For example, stimulator implants have been used to modulate and synchronize bladder and sphincter function via two different alternately stimulated muscles, as described in U.S. Pat. No. 6,393,323 issued to Sawan et al., on May 21, 2002. In some cases, stimulator implants may amplify volitional control of a specific muscle by electrode detection of early muscle contraction followed by a stimulatory pulse sent to the electrode as described in U.S. Pat. No. 6,354,991 issued to Gross et al., on Mar. 12, 2002. One embellishment to this technique is biphasic stimulation with a first anodal sub-threshold stimulation followed later in time by a cathodal stimulation for the same muscle as described in U.S. Pat. No. 6,343,232 issued to Mower et al., on Jan. 29, 2002. Still further improvements include, for example, the use of electrodes that remain at a desired implantation site and that accommodate expansion of muscle during muscle flex, such as Peterson-like electrodes and flexible electrode leads.

These advances are helpful but generally do not address sufficiently the control of specific cartilage, tissue or bone movements, which require the coordinated action of multiple muscles. For example, at least 12 muscles are involved in moving the hyoid bone. Proper control of this movement is particularly important due to the consequences from failure of movement of this bone to raise the larynx to protect the airway and open the upper esophageal sphincter to clear liquid or food from the hypopharynx. That is, normal swallowing involves hyolaryngeal muscle contractions that synchronize with and control the opening of the upper esophageal sphincter. The apparently intricate orchestration of muscle movements needed for this double action has not been previously controlled by stimulation of hyoid associated muscles through implanted electrodes.

Some attempts to control upper respiratory muscles used for swallowing have targeted the hyoid associated muscles through exterior skin electrical contact. For example, Freed et al. have described a non-invasive method and apparatus that continuously stimulates the skin surface to assist patients in initiating a swallow (U.S. Pat. Nos. 5,725,564; 6,104,958 and 5,891,185). The Freed et al. device is a temporary basis sensory stimulation tool for early rehabilitation of stroke patients that have difficulty initiating swallowing behavior. This device may have some value for swallowing rehabilitation therapy. However, no suitable description of a chronically implanted (i.e. implanted for multiple stimulations) neuroprosthestic system exists for long term prevention of aspiration during swallowing in patients who have not been able to take food or liquids by mouth following unsuccessful rehabilitation. The Freed et. al. rehabilitation device is not appropriate for patients with a chronic disorder that require enteric feeding due to the risk of aspirating food.

Another problem with the Freed et al., technology is the inability to produce direct movement or muscle contraction. More specifically, the Freed device does not demonstratively elevate the larynx, move the hyoid bone or open the upper esophageal sphincter. It appears that this device and the method of its use operate by creating a sensory input without directly causing any muscle contraction or other action involving the larynx. This research group commented on the latter limitation to their method, stating "[m]uch research is required to determine whether ES (electrical stimulation), applied at a sensory level in our study, works via a peripheral nerve, a direct effect on the small muscles, the central nervous system, or a combination of these factors." (Freed et al. *Respiratory Care,* 46: 466-474, 2001). Accordingly, although the Freed group seems to have made some progress using an externally applied electric current, a major conclusion from their limited success is that a suitable route for direct control of the muscles involved in swallowing remains unknown.

Despite the hints that basic research is needed in this area, dysphagia conceivably might be alleviated by direct control of muscles that are no longer receiving the correct signals from the brain. However, the route for alleviating dysphagia by direct control of muscles has not been tried with convincing success. Although Bidus et al. showed that stimulation of the thyroarytenoid vocal fold muscles in the larynx with percutaneously inserted hooked wire electrodes could close the glottis and improve the voice in patients with abductor spasmodic dysphonia (Bidus et al. *Laryngoscope,* 110:1943-1949, 2000), no synergistic production of laryngeal elevation and opening of the upper esophageal sphincter were attempted.

Another group found that chronic stimulation of canine thyroarytenoid vocal fold muscles with Peterson-like type electrodes could close the glottis intermittently during 6 months of chronic implantation in the canine (Ludlow et al. *Journal of Artificial Organs,* 23:463-465, 1999; and Ludlow et al. *Muscle and Nerve,* 23:44-57, 2000). However, the studies did not address elevation of the larynx or opening of the esophageal sphincter. More pertinently, individual laryngeal muscle stimulation in humans has been explored but synergistic anterior movement of the hyoid bone with simultaneous opening of the upper esophageal sphincter, as needed to prevent aspiration, were not examined. Furthermore, although at least twelve muscles are known to have involvement in swallowing, there has been no clear understanding of which muscles may predominate or even if proper swallowing requires coordinated contraction of all twelve or more muscles. In addition, the system may be complicated in unexpected ways by individual differences. For example, the geniohyoid, mylohyoid and digastric muscles are used selectively by different individuals, with some using all three muscles at the onset of swallowing, and others using different pairs (Spiro et al., Laryngoscope 104: 1376-82 1994). In addition, the temporal association between submental muscle contractions differs across individuals (Hrycyshyn et al., Am. J. Anat. 133: 333-40 1972). Thus, despite work in this area, muscular control by imbedded electrode(s) to coordinately control a solid internal body part such as a cartilage, tissue or bone through two or more muscles and thereby emulate normal synergistic movement has not been possible.

SUMMARY OF THE INVENTION

The shortcomings of electrode control of internal solid body part movements summarized above are alleviated by embodiments of the invention. One such embodiment provides a method of synergistic production of movements during speech, swallowing or voice production, comprising: chronic implantation of at least two intra-muscular stimulators into different muscles involved in the upper airway and vocal tract, chronic implantation of a signal generator that generates electrical pulses to at least two intra-muscular stimulators; wherein electrical pulses from the signal generator activate at least two muscles to produce the synergistic movement control during the activity. Another embodiment provides a method of moving the hyoid bone, and/or parts of the upper airway and/or vocal tract within an animal by two or more different controlled muscles, comprising: implanting at least one electrode into each of two or more different muscles; electrically connecting each electrode to a indwelling subcutaneous signal generator capable of generating a pattern of stimulation; and energizing the controlled muscles at the same time by the signal generator to synergistically move the parts of the upper airway, hyoid or vocal tract. Yet another embodiment provides a method of simultaneously moving the hyoid bone and opening the upper esophageal sphincter within an human via at least one muscle attached to the hyoid bone, comprising: implanting at least one electrode into each of two or more said muscles; electrically connecting each electrode to a signal generator capable of generating a complex pattern to activate the muscle attached to the electrode; and energizing electrodes in at least two of the muscles at the same time with the signal generator, thereby synergistically moving the hyoid bone and/or opening the upper esophageal sphincter. Yet another embodiment provides a system for moving a cartilage within an animal, comprising: a first electrode implanted in a first muscle attached to the cartilage; a second electrode implanted in a second different muscle attached to the same cartilage; and a signal generator that sends pulses to the first and second electrodes at the same time; wherein the pulses from the signal generator energize the first and second muscles to effect a synergistic movement in the cartilage that exceeds the movements made by pulses sent to the muscles at separate times. Yet another embodiment provides a system for long term control of stimulation during swallowing of a human with dysphagia comprising: at least two intramuscular electrodes; a signal generator connected to two or more electrodes that outputs energy to the electrodes according to a determined pattern; a power supply that provides energy for the signal generator; and a switch operable by the implanted human that controls the signal generator, wherein the electrodes are imbedded in at least two different muscles of the human's hyolaryngeal complex that control hyoid movement and laryngeal elevation to protect the airway and operation of the switch by the implanted human causes contraction of the at least two different muscles to prevent aspiration during swallowing. Yet another embodiment provides a method of independent long term control of stimulation during swallowing to prevent aspiration in chronic dysphagia in a human patient comprising: implanting at least one electrode(s) into at least two different muscles of the patient's hyolaryngeal complex; implanting a controller containing a processor into the patient; providing a patient operable switch that triggers the controller from outside the human body. Still another embodiment provides a method of independent long term control of speech and/or voice production in a human patient with speech or voice disorders comprising: implanting at least one electrode(s) into at least two different muscles of the patient's vocal tract complex; implanting a controller containing a processor into the patient; and providing a patient operable switch that triggers the controller from outside the human body. Further embodiments will be appreciated by a reading and understanding of the specification.

DESCRIPTION OF THE DRAWINGS

Figure one depicts a representative videofluorographic image.

Figure two depicts hyoid anterior movement data relative to the cervical vertebra resulting from muscle stimulation as a percentage of the normal hyoid anterior movement that occurs during swallowing.

Figure 1:
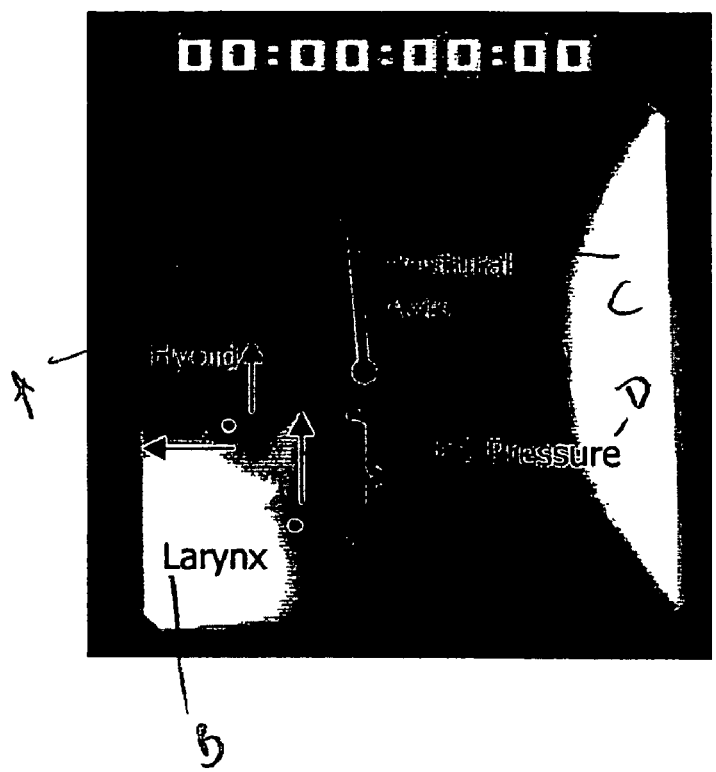

Figure three depicts the degree of hyoid elevation movement as a result of muscle stimulations depicted as a percentage oft normal hyoid elevation that occurs during swallowing.

Figure four depicts the degree of laryngeal elevation relative to that occurring during swallowing.

Figure five shows manometry tracings of pressure change during combined muscle stimulations and during swallows of various bolus size and consistencies.

Figure six shows a correlation of change in pressure with anterior movement of the hyoid due to geniohyoid muscel stimulation either bilaterally or in comboination with other muscles.

Figure seven shows the onset of mylohyoid muscle (MH) activation preceding the thyrohyoid (TH) and levator veli palatini (LVP) during swallowing.

Figure eight shows onset of the relationship of mylohyoid, thyrohyoid and levator veli muscle activation during swallowing relative to subjects' timing of button press (at 0) for stimulation over 9 trials.

Figure nine depicts plots of the mean duration of mylohyoid (MH) and thyrohyoid (TH) activation in 9 subjects prior to stimulation (baseline) and following 10 stimulation trials (post).

Figure ten depicts plots of mean integrals of mylohyoid (MH) and thyrohyoid (TH) activation in 9 subjects prior to stimulation (baseline) and following 10 stimulation trials (post).

Figure eleven depicts plots of mean intervals between activation of the mylohyoid (MH) and thyrohyoid (TH) in 9 subjects prior to stimulation (baseline) and following 10 stimulation trials (post).

DETAILED DESCRIPTION OF THE INVENTION

In contrast to many expectations in this field, it was surprisingly discovered, using a 12 muscle model system in the human associated with the pharyngeal phase of swallowing, that neuromuscular stimulation of only 2 of the muscles yields a large proportion of normal desired movement for a body part (the hyoid bone). In contrast to single muscle stimulation, the two muscles could be controlled together to yield two synergistic actions to prevent aspiration during swallowing in humans: 1) simultaneous hyoid elevation and laryngeal elevation to protect the airway; and 2) opening of the upper esophageal sphincter to clear liquid or food from the hypopharynx. Most surprisingly, selective hyolaryngeal muscle stimulation alone was found to produce both actions simultaneously in a manner that can prevent of aspiration in chronically dysphagic patients. Furthermore, stimulation of the geniohyoid muscle, in combination with at least one other muscle in this muscle group was particularly effective in generating the synergy.

It was also discovered that, contrary to expectations, an individual with electrodes implanted in two muscles successfully can learn proper coordination of stimulation with movement of an internal body solid (bone or cartilage) over a short time period. That is, a user quickly can learn to self-initiate hyolaryngeal muscle stimulation and to coordinate the electrode driven synergistic actions with the onset of their own swallowing. This coordinate control of voluntary muscle movement with an electrode driven system can prevent aspiration while eating and thus provides independence from caregivers. In an advantageous embodiment such control is exerted by a simple hand switch or other switch activated by a body movement in combination with regular body movement(s) associated with eating.

It was further discovered that multiple indwelling intramuscular electrodes placed in two or more muscles of the upper airway musculature can be combined with signal generator(s) inside the body, to exert synergistic motion controlled by an external device communicating either through radio waves or electromagnetically with the implanted signal generator. Yet another discovery is the ability to calibrate electrode activated body movements to compensate for vagaries in electrode placement within the upper respiratory muscles and the user's particular movement deficiencies thereby decreasing the complexity of electrode placement and improving system reliability. This basic technique can slash dramatically the complexity and cost of establishing a control system and maintaining that control system over time.

Without wishing to be bound by any one theory of this embodiment of the invention, it is believed that coordinate control of two or more muscles is made feasible with as little as one electrode in each muscle governed by a signal generator to make a specific signal or signal train appropriate for each electrode, after correcting for inter-electrode differences such as type of electrode, location of the electrode in/on the muscle, localized condition of the muscle at or near the implantation site, depth of implantation of the electrode, condition of the insulation of leads that connect the electrode to the signal generator, and so on.

Advantageously, to govern the signal generator and/or controller it is best to generate one or more reference signals and then detect the effect of the signal on subsequent muscle movement. From the information detected, the signal is then altered to a more appropriate type by signal processing. The generation of reference signal(s) may be repeated as needed. Preferably this sequence is carried out a) autonomously by an implanted device upon the signal generator or a controller which governs the signal generator, such as a timer to prompt muscle stimulation, b) by an implanted device that receives detected information obtained from outside the body and uses that information to modify the signal generator or a controller which governs the signal generator, or by c) external timing, external detection of muscle activity or movement information and external processing of information, after which the signal generator or a controller which governs the signal generator is instructed or directly controlled to modify the electrode signal. In the first case a), a feedback loop may be used such as an electrical signal detected in response to muscle movement by another receiving electrode in a muscle. In the case of external calibration as in b) and c), an external detector such as a piezoelectric sensor often may be used to measure the degree and quality of body movement. Example 1 describes a representative use of a video system to detect the effect of the signal on subsequent muscle movement that measures X+Y displacements as the formation of images within the visual field of the detector and which are analyzed by a computer to determine the effect of an electrode stimulation.

In a particularly desirable embodiment, Peterson-like type intramuscular electrodes are surgically inserted into at least two muscles that attach to the same solid body, such as a cartilage and/or bone involved in the upper respiratory and swallowing systems. The electrodes optionally interface with an implantable system. The implanted system, when operational and calibrated, provides at least two axis control of the attached solid body upon excitation of at least two muscles by short trains of electrical stimulation with programmable rates, pulse widths and durations of stimulation over a wide range of current levels. In a particularly desirable system, the fully implanted signal generator accepts a command from outside the body to trigger an electrode driving pulse.

Two Muscle Activation for Synergistic Results

Many muscle groups, particularly those associated with the upper respiratory and swallowing systems include muscles that, rather than act in opposing force vectors, create forces that are applied to the attached solid body in force vectors that modify the resultant movement with respect to each other. In advantageous embodiments two muscles (or pairs of muscles) act relative to each other to modify the resultant movement trajectory to generate a complicated movement of the commonly attached solid body. For example, within the 12 muscle system that moves the hyoid bone as part of swallowing, it was surprisingly discovered that neuromuscular stimulation of only 2 of the muscles yielded most (80% or more) of a normal movement. In contrast to single muscle stimulation, the two muscles could be controlled together to yield the synergistic result. Most preferably at least one of the muscles is a geniohyoid muscle that contracts with a force vector that optionally is modified or augmented by the force vector of the second muscle.

In another embodiment three muscles are stimulated, wherein two of the muscles may result in force vectors that are applied at angles to one another in their effects upon the target structure. The third muscle may form a force vector that may modify or augment the forces vectors of either or both of the first two muscles. In yet another embodiment, a system of three or more muscles is calibrated by determining a desired or optimum electrode stimulation pattern to two muscles with force vectors acting at angles to one another on the target structure and then by adjusting electrode stimulation to a third muscle to achieve a desired effect. In yet another embodiment, a pair of muscles that oppose each other (do not create perpendicular force vectors) are stimulated alternately to a desired frequency, and at least one other muscle that assumes a perpendicular force vector with the first two is stimulated in different ways to determine an optimum effect.

Muscle Groups for Biaxial Cartilage or Bone

It was surprisingly discovered that electrode excitation of muscle attached to the center or near the center of a biaxial cartilage, tissue or bone (the hyoid bone), when combined with electrode excitation of a muscle attached further to one side of the center of the biaxial cartilage, tissue or bone yields synergistic movement of the cartilage or bone. Exciting this combination of two muscles caused more desired movement compared with excitation of each muscle alone. In the hyoid bone system for example, 12 muscles either attach to and/or control movement of a biaxial hyoid bone. Excitation of the near-center attached geniohyoid muscle was a key to producing the best synergistic anterior movement of the hyoid bone with simultaneous opening of the upper esophageal sphincter. That is, a combination of electrode excitation of a near-center attached muscle and an off center attached muscle caused multiple synergistic movements. Embodiments specifically contemplate synergistic movement of other biaxial cartilages and bones in the body, through electrode stimulation of as few as two muscles according to this pattern.

Greater Flexibility in Electrode Placement

In a controlled demonstration of an embodiment, pairs of muscles from different individuals were stimulated using different voltages, currents, pulse patterns and periodicities. Often, a particular stimulated muscle in one individual would react differently to the same electrode pulse in the same muscle in another individual. Despite these differences, successful synergistic movement was obtained in different individuals by compensating for the different electrode stimulation responses by combining stimulation of different intramuscular electrodes simultaneously. Preferably compensation is carried out by adjusting the electrode stimulation to a given muscle and obtaining feedback regarding the effect on the muscle. The feedback may, for example, come from sensory observations of the implanted individual, and preferably includes data from an objective measurement of muscle movement, such as from a two-axis digital image of a body part taken from outside the body. In an embodiment, the effect of an electrode stimulation on a muscle is determined by direct electrophysiological measurement from another electrode imbedded at a separate location in the same muscle.

By way of example, a particular muscle may be excited by an electrode with a constant electrical pulse chain of 2 milliamperes. An associated movement is measured with a digital video camera that images the surface of the overlying skin or fluoroscopy. The skin/structure optionally is marked beforehand with a color or pattern for easier image analysis. After determining movement of the skin/structure in response to 2 milliamperes, the current is increased to 3 milliamperes, 4 milliamperes, and so on, and the effects on the skin/structure displacement determined. This process is repeated, by varying other parameters such as current, pulse length, frequency of repetition until enough information is obtained to determine a final pulse type. A calibrator pulse and measurement of effect may also be made and repeated over a long time period (ex. one per day, once per week, once every couple of months) to adjust the pulse quality as needed for compensating for long term changes in muscle strength, electrode position and depth, and so on.

Preferred Procedures for Practicing Embodiments of the Invention

Muscles—Virtually any muscle in the body that is large enough to accept an electrode may be used in embodiments of the invention. Most preferred are striated muscles that attach to ligaments and tendons which move bones, or to cartilage. Most preferred for desirable embodiments are the use of two or more muscles engaged in the upper respiratory and swallowing systems. Generally, the most preferred muscles can be considered as falling into three types, categorized as muscle groups that work together for three different physiological functions: swallowing, speech and voice. One type creates swallowing motion. This group of muscles includes the mylohyoid, thyrohyoid, geniohyoid, hyoglossus, palatopharyngeus, cricopharyngeus, inferior constrictor, superior constrictor, anterior and posterior bellies of the digastric, genioglossus, temporalis, levator veli palatini, tensor veli palatini, palatoglossus, inferior longitudinal and superior longitudinal muscles of the tongue, styloglossus, thyroarytenoid, lateral cricoarytenoid, and interarytenoid muscles. According to embodiments of the invention, intramuscular electrode combinations of two, three, four, five, six, seven, eight, or more of these may be used to effect a swallowing motion, to enhance swallowing motion, to initiate swallowing motion, to augment swallowing motion, and/or to produce or enhance part of a complex pattern of movement during swallowing. Of these muscles, most preferred are two or more muscles selected from the group consisting of the bilateral mylohyoid muscle(s), the bilateral thyrohyoid muscle(s), the bilateral geniohyoid muscle, the unilateral mylohyoid muscle(s), the unilateral geniohyoid muscle(s), the unilateral thyrohyoid muscle(s), the geniohyoid and thyrohyoid muscle combination, the mylohyoid and thyrohyoid muscle combination, the geniohyoid and the mylohyoid muscle combination. Most preferred in this context is a combination of the geniohyoid muscle with at least one other muscle, as it was unexpectedly discovered that electrode stimulation of the geniohyoid and stimulation of any of the hyolaryngeal muscles gave stronger hyoid bone movement compared with stimulation of two other or separate hyolaryngeal muscles.

The second type creates motion needed for speech. This group of muscles includes the lateral pterygoid, medial pterygoid, anterior belly of the digastric, obicularis oris, buccinator, zygomaticus, depressor labi inferior, mentalis, levator labi superior, genioglossus, inferior longitudinal and superior longitudinal muscles of the tongue, styloglossus, anterior belly of the digastric, temporalis, levator veli palatini, tensor veli palatini, palatoglossus, styloglossus, thyroarytenoid, lateral cricoarytenoid, posterior cricoarytenoid, cricothyroid, stylohyoid, and interarytenoid muscles. According to embodiments of the invention combinations of two, three, four, five, six, seven, eight, or more of these may be used with electrodes to effect speech, to enhance speech, to initiate speech, to augment speech, and to produce or enhance part of a complex pattern of movement during speech.

The third type of muscles produce voice. This group of muscles includes the thyroarytenoid, lateral cricoarytenoid, posterior cricoarytenoid, cricothyroid, sternothyroid, and interarytenoid muscles. According to embodiments of the invention combinations of two, three, four, or more of these may be used with electrodes to effect a voice, to enhance voice, to initiate a voice, to augment voice, and to produce or enhance part of a complex pattern of movement during a vocalization.

A "controlled muscle" is a muscle that has an electrode in contact with the surface (on the muscle surface in electrical contact with muscle cell sarco lemma) or imbedded within the muscle and that can respond to an electrical signal applied to the electrode. The controlled muscle participates in coordinated cartilage, tissue or bone movement. "Coordinated cartilage, tissue or bone movement" means that the cartilage and/or bone moves in a direction and by a distance as determined by the action of at least two controlled muscles. In many cases the direction of coordinated movement will differ from the direction of contraction of each controlled muscle but will reflect the action of the coordinate operation of the muscles working together at the same time.

Electrodes—Although the term "electrodes" is used throughout, another, more descriptive term with the same meaning is "intra-muscular stimulator." At least one intramuscular electrode is placed into a chosen muscle by any of a number of procedures. For muscles that are close to but underneath the skin surface, optimal electrode position and depth may be estimated using visually identifiable anatomical landmarks during surgical exposure. These placement parameters may be further tested by neuromuscular stimulation, for example with 0.2 to 10 milliamperes, 50 to 500 (preferably 200) microsecond biphasic pulses at 10 to 75, preferably 30 hertz frequency and lasting about 1-3 seconds with a monopolar simulating needle electrode paired to a reference electrode elsewhere in/on the subject's body. A bipolar electrode also may be used for better local control. Electrodes may be positioned deep within a muscle or deep within the body by manipulating the electrode while monitoring the muscle and electrode location. Electrodes may be positioned in a muscle during the course of an operation that exposes the muscle temporarily, thus allowing direct insertion by sight.

An electrode may be of any dimension or size as limited by the muscle bulk. A variety of electrodes are known, as for example described by Handa et al. IEEE Trans Biomed Eng 1989;36(7):705; Waters et al. J Bone Joint Surg June 1985; 67-A(5):792-3; Strojnik et al., Scand J Rehabil Med 1987;19: 37-43; Stanic et al., Scand J Rehabil Med 1978;10:15-92; Marsolais et al., J. Rehabil. Res. Dev. 1986;23(3):1-8; Mortimer et al., Ann Biomed Eng 1980;8:235-44 and Scheiner et al., IEEE Trans Biomed Eng 1994;41(5):425-31, the contents of which pertaining to electrode design and placement are particularly incorporated by reference. In many cases a electrode may be inserted through the skin, is sterilized and directed towards the endplate region of a target muscle. A polypropylene core electrode having enhanced durability may be used, as described in Daly et al., J. Rehabil. Res. Dev. 2001; 38(5). Multiple electrodes may be implanted within the largest muscles or within different compartments of the same muscle and optionally controlled by common or separate electrical signals. Each electrode typically is electrically connected to a signal generator by a conductive pathway such as an insulated wire lead. A Peterson-like electrode is particularly preferred.

Signal Generator—The term "signal generator" broadly refers to circuitry implanted within the body and which outputs electrical pulses that cause electron movement suitable to impress a voltage at the attached electrode(s). The signal generator optionally may comprise signal processing circuits, a computer, a trigger signal receiver such as a radio receiver, a signal transmitter such as a radio transmitter and/or internal power supply. An electrical signal generated by the signal generator typically flows at a 0.1 to 25 milliampere rate and more usually between 0.5 to 10 milliamperes at a pulse shape, polarity and repetition rate as determined for each controlled muscle. The signal generation circuitry itself can be as simple as a hard wired circuit that is triggered as desired, may be controlled by a microprocessor or may be simply a microprocessor output with minimum signal conditioning such as adding capacitance or use of multiple conductive shunts. A wide variety of circuits and (if applicable) stored programs may be used to generate the signal. In many embodiments the signal generator will control more than one electrode simultaneously.

The signal generator(s) in many embodiments is powered by an internal power source such as a high capacity capacitor or a rechargeable electrochemical battery. The signal generator and power source (if combined together) most advantageously is inserted into the body as a single encapsulated unit a short distance away (generally less than 50 cm, preferably less than 25 cm, more preferably less than 15 cm) from the controlled muscles. In such event, the capsule has a surface that is biocompatible with the interior of the human body and optionally can be both recharged and triggered by energy (electromagnetic radiation, alternating magnetic flux etc.) from outside the skin.

An implantable device generally has a controllable output and small size, and comprises a signal generator with power supply that is recharged through the skin after implantation, Most preferably, the implantable device allows autonomous adjustment of the signal generator to changing needs (such as in response to differences in muscle response). Most desirably the implantable signal generator includes processing circuitry to generate a complex waveform. A "complex waveform" generated by the signal generator can be as simple as a monophasic/biphasic square wave or as detailed as an intermittent pulse train of microprocessor derived waveform shape of varying intensity, and includes as a minimum, all of the waveform types now available and used by workers in this field. In many embodiments the "signal generator" is a single implantable device that controls multiple electrodes in multiple muscles. However, the term "signal generator" also refers to multiple discrete devices, the output of which may be coordinately controlled to effect the desired muscle, tissue, cartilage and/or bone movement(s).

In embodiments, two or more controlled muscles are activated by signals from the signal generator(s) that activate electrodes in the muscles and trigger one or more action potentials in the sarco lemma of the muscles. Preferably the muscles are energized at the same time by the signal generator. The term "at the same time" refers to muscle contractions caused by the signals and means that the induced muscle contractions occur at overlapping or identical time interval(s). In many cases the signal generator outputs a pulse stream of electrical signals to the controlled muscles at overlapping time periods to bring about this coordination. In some cases, depending on the type of muscle, the muscle's dimensions and the location of the electrode(s) one signal may start before another to compensate for these differences, in which case at least part of the pulse train and/or the effects overlap. This condition of "overlap" means "at the same time."

In embodiments, an initial muscle movement induced voluntarily by the user's nerves or by the signal generator is detected by a feedback circuit, which may include a detector that is attached to the signal generator. The detector may be any device that responds to either muscle contraction, or to nerves such as efferent nerves that conduct signals to a muscle from a local reflex or from the brain. The attached detector may be an electrode, which may be used solely for sensing, or may be a dual purpose sensing/output electrode. The detector electrode may respond to a weak initial muscle contraction by sending an electrical signal picked up from the contraction to a separate implant not directly wired to the signal generator, or to the first signal generator. In response to this feedback the signal generator(s) can start a coordinated muscle contraction. In many cases an individual switches the signal generator to create a coordinated muscle movement by a conscious command, such as by pushing a button or speaking to a computer.

Compensating for Electrode Placement, Alteration in Response

It was discovered in the study summarized in Example 1 that stimulation of individual muscles results in different amounts of laryngeal elevation in different individuals. For example, bilateral thyrohyoid stimulation achieved the greatest laryngeal elevation in one participant while in another it produced the least effect. Without wishing to be bound by any one theory of how this embodiment of the invention operates, it is thought that normal variation in anatomy underlie some individual differences and that variation in electrode placement from participant to participant is a larger factor. For example, electrode stimulation close to nerve endings has a greater effect than distant stimulation and stimulation to some muscle areas may produce movement of a different direction than stimulation to other areas of the same muscle. Accordingly, one embodiment is a case-by-case method that accommodates such differences by determining an optimal signal for each individual implantation site.

This embodiment compensates by optimizing each implanted electrode in a specific muscle using feedback from the electrode effects on that specific muscle. After each electrode pulse signal is optimized, the different muscles are activated together to form a synergistic effect on their common-attached solid or soft body part. In one such embodiment a needle such as a monopolar needle is placed as determined physiologically, based on predicted patterns of movement during stimulation. For example, mylohyoid stimulation may be defined as that which causes both thyroid prominence elevation and submental tissue retraction. Geniohyoid stimulation may be defined as that which causes an inferior-anterior bulking of submental tissue without producing tongue movement or jaw lowering. Thyrohyoid stimulation may be defined as that which causes elevation and a slight diagonal twisting of the thyroid prominence contralateral to the side of stimulation. A suitable pulse type (polarity, shape, periodicity, impedance, voltage, current and so on) is determined by asserting a pulse to a needle in a particular muscle followed by detecting the effect of the pulse on the above defined movement. Once the desired physiological action is produced, the monopolar needle may be removed and an electrode inserted in its place, using, for example a carrier needle.

According to another embodiment, following placement and use, electrode system performance is checked analogously to the initial optimization procedure, and further optimized by, for example, increasing stimulation amplitude until a satisfactory maximum effect is achieved. In another embodiment, a test of a reference pulse is repeated at various time intervals, such as once an hour, one a day or once a week, and the effect of the reference pulse on the physiological movement monitored. The pulse may be altered, (by changing its frequency, duration, amplitude etc.) to compensate for performance drift that may occur in the system. In a desirable embodiment the patient user may carry out this calibration autonomously or with a caregiver, using visual feedback or a motion detector attached to a portion of the body. The calibration results may be sent to a medical practitioner by telephone or other device, to assist monitoring the performance of the device. In a desirable embodiment the signal generator is programmed to respond to drift in performance by altering amplitude and/or another parameter upon receiving the calibration results.

Working Examples: Stimulation of Muscles to Counteract Aspiration in Dysphagia

Aspiration in dysphagia arises from a number of causes, such as pathologically reduced or delayed laryngeal elevation (Lundy et al., Otolaryngol. Head NeckSurg. 120: 474-8 1999), either as the primary swallowing dysfunction, or as a part of a composite of kinematic and temporal deficiencies (Sundgren et al., Br. J. Radiol. 66: 768-72 1993). Reduced elevation may result from traumatic brain injury or cerebrovascular accident affecting central control, partial laryngeal resection, tissue injury caused by external-beam radiation treatment of the larynx, or nerve injury during cervical spinal surgery with an anterior approach as reviewed by Burnett et al. (Journal of Applied Physiology, 94:128-134, 2003). Each of these pathologies may be addressed by one or more embodiments described herein.

Muscles that carry out swallowing activity were separately stimulated in a series of studies that demonstrate how stimulation of only two muscles provides up to 80% of normal movement, which is sufficient to initiate and control swallowing. The working example further demonstrates that, contrary to expectations, an implanted subject can coordinate the onset of timing of stimulation with his or her own swallow and that stimulation did not alter the pattern of their own swallowing timing. Thus, although automatic triggering devices are contemplated in some embodiments of the invention, working examples were prepared that show the capability of self-timing, in accordance with preferred embodiments relating to swallowing. Although not explained in as much detail, corresponding embodiments exist for control of speech and control of voice, based on stimulation of two or more muscles within the groups of muscles identified for these further activities. Yet another set of embodiments embrace the use of chronic simulation to improve muscle tone and performance for the three activities of swallowing, voice and speech, based on electrode stimulation of muscles engaged in these respective activities.

Figure 2:
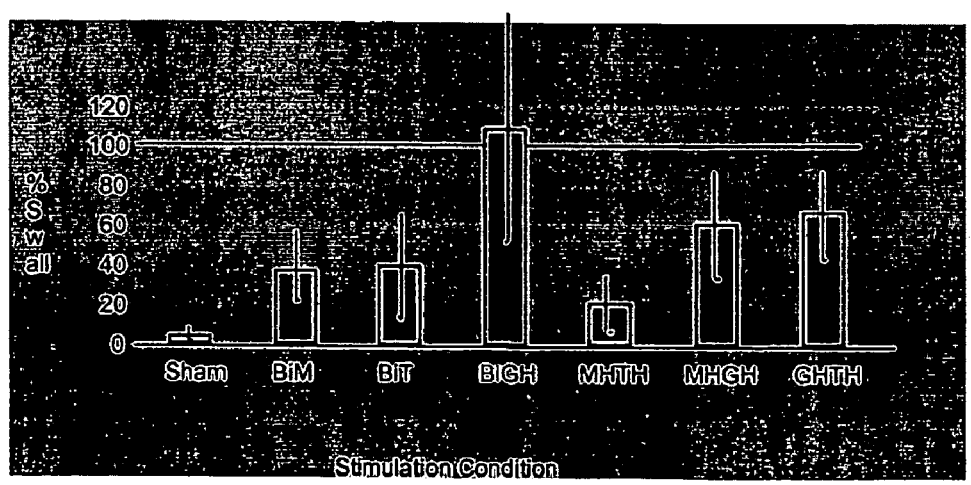

As described in Example 1 below, the velocity of thyroid prominence movement induced by the combined stimulation of two muscles averaged 80% of the velocity achieved during a 2 ml wet swallow. Data presented in Example 2 indicate that that implantation of the geniohyoid and mylohyoid muscles have the greatest potential benefit for augmenting or initiating hyoid and laryngeal movement for swallowing. For example, FIG. 2 shows hyoid bone anterior movement relative to cervical vertebra as a percent of hyoid anterior movement relative to cervical vertebra during swallowing of 5 ml of liquid. The videorecordings of fluoroscopy were carried out during muscle stimulation at rest. This figure shows a clear benefit of bilateral geniohyoid stimulation compared to that of the other muscles studied. The greater degree of anterior motion seen with bilateral geniohyoid stimulation (compared to swallowing) demonstrates significant potential benefit of bilateral geniohyoid stimulation to effect anterior motion of the hyoid bone.

Figure 3:
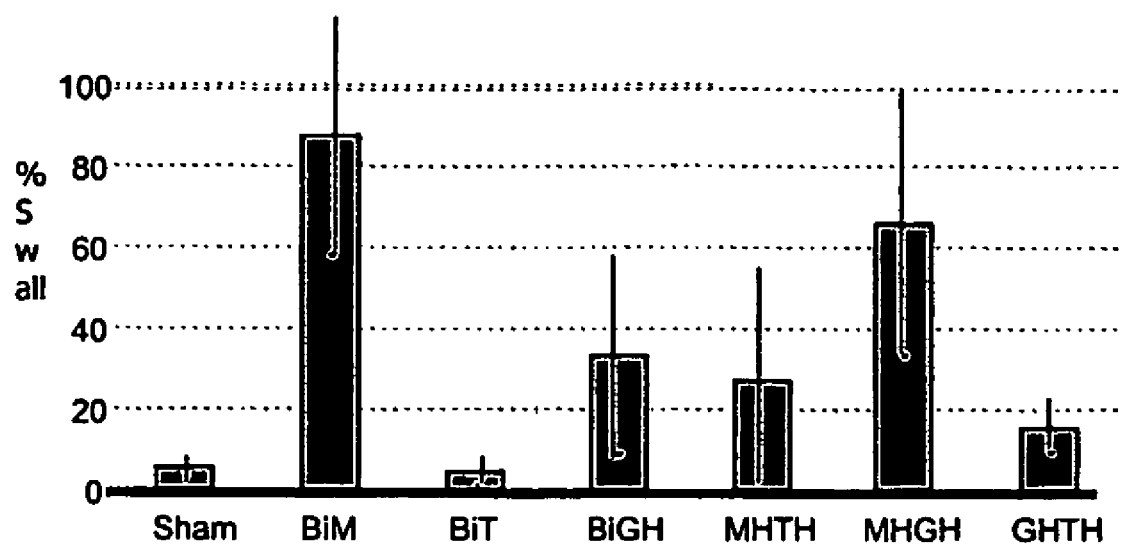
Figure 4:
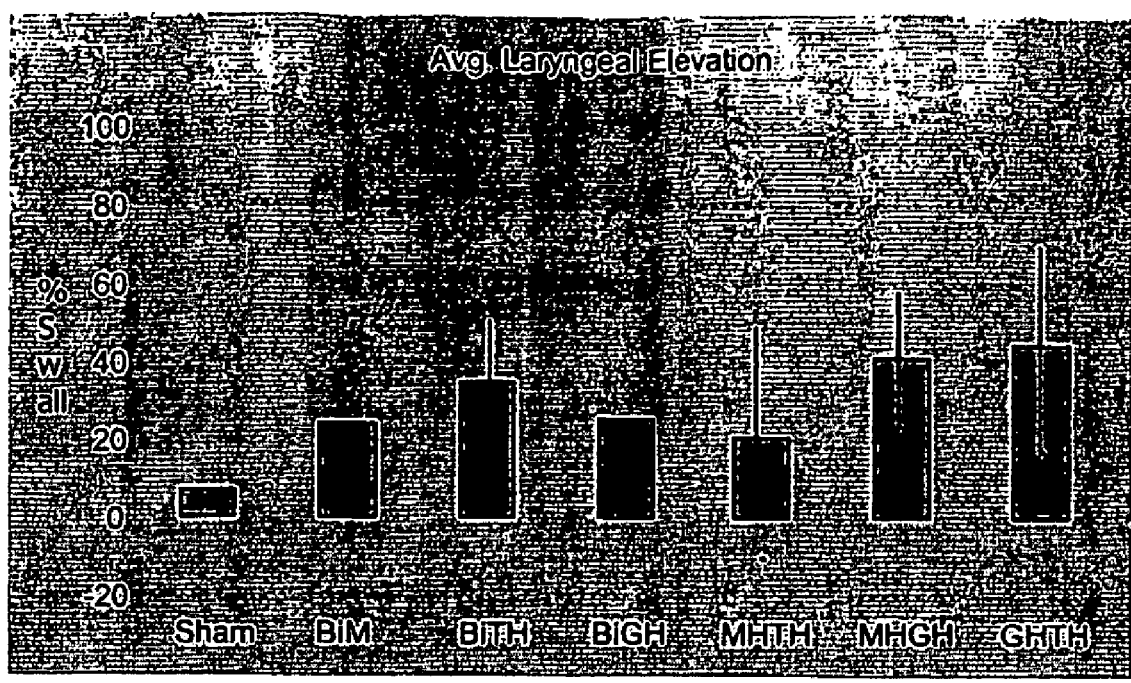

FIG. 3 shows hyoid elevation relative to the cervical vertebra as a percent of hyoid elevation that occurs during normal swallowing. FIG. 4 shows elevation of the subglottic air column relative to the cervical vertebra. These latter results show that all muscle stimulation conditions elevated the subglottic air column by approximately 30%. This conclusion comports with previous findings obtained by tracking the movement of the thyroid prominence.

The results of Example 2 show that stimulation of the mylohyoid and geniohyoid muscles most affects the 3 monitored movements: the hyoid anterior movement (FIG. 2), hyoid elevation (FIG. 3), and laryngeal elevation (FIG. 4). Combined geniohyoid, combined mylohyoid and/or combined mylohyoid and geniohyoid muscle stimulations can create movements that exceed normal swallowing hyoid anterior movements, or 80% of hyoid elevation and close to 50% of laryngeal elevation.

Although laryngeal protection can be provided by elevating and closing the glottis through neuromuscular stimulation, it is essential to also open the cricopharyngeus for the bolus to be cleared from the hypopharynx. Otherwise, the bolus will remain in the pharynx and poses a risk for post swallow aspiration. Example 3 was carried out to determine the duration and extent of stimulation required to open the upper esophageal sphincter through laryngeal elevation. In this study, simultaneous manofluorography measurements assured accurate placement of the manometer in the upper esophageal sphincter and correspondence of pressure changes in the upper esophageal sphincter with the extent of laryngeal elevation during neuromuscular stimulation. This allowed determination of the extent of sphincter opening by changes in pressure.

It was also found that (see FIG. 5) a pressure drop in the UES occurs during bilateral mylohyoid, bilateral geniohyoid and combined mylohyoid and geniohyoid stimulation. This figure shows manometry tracings of pressure change during combined muscle stimulations (top box) and during swallows of various bolus sizes and consistencies (bottom box). Bilateral thyrohyoid and mylohyoid and thyrohyoid stimulation, however, increased UES pressure in this subject. A drop in pressure indicates a reduction in closing pressure within the UES. The pressure and videofluoroscopy recordings were synchronized and digitized to allow for coincident measures made of change in hyoid position and decrease in pressure.

Figure 6:
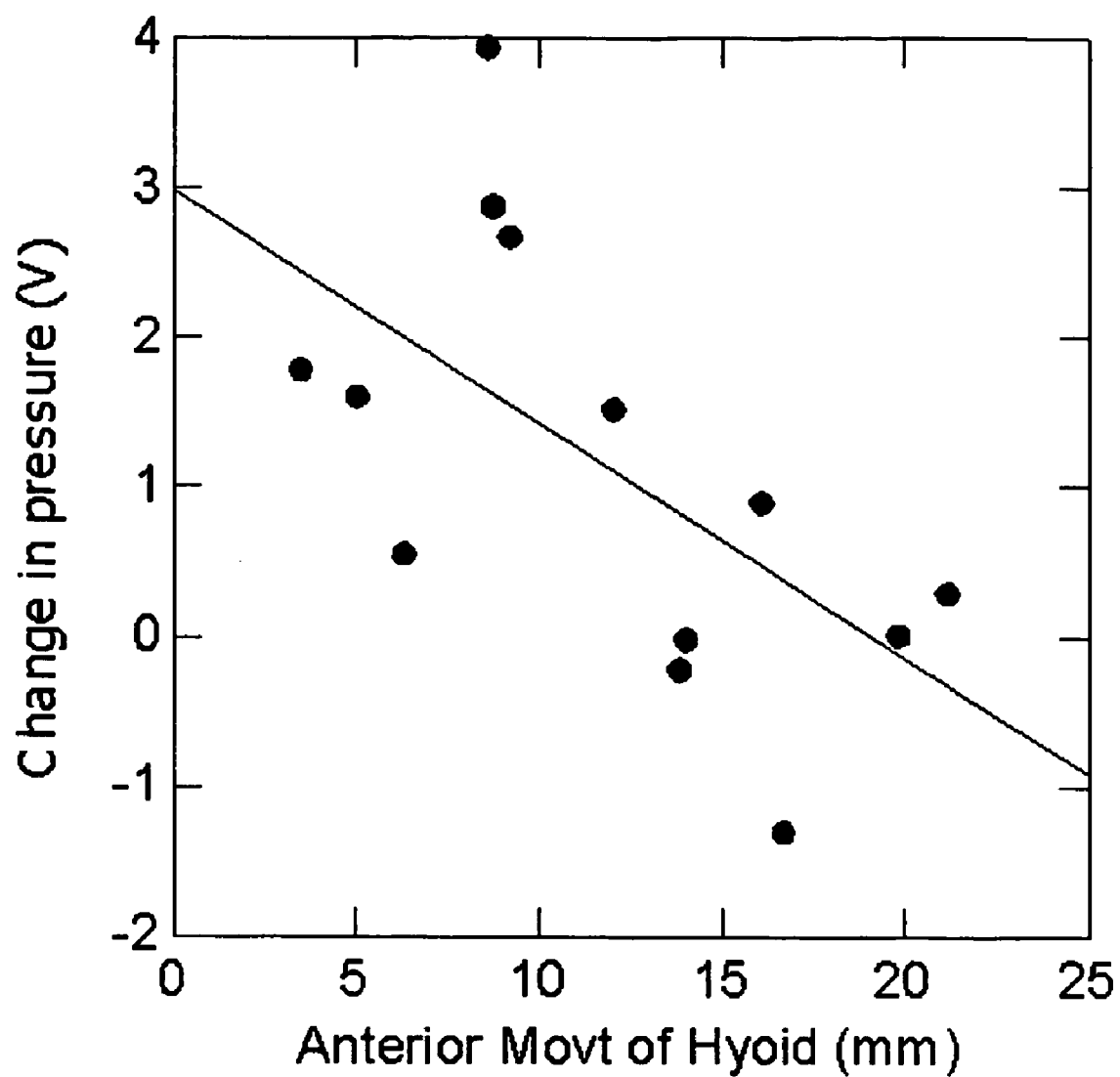

FIG. 6 shows a relationship between anterior movement of the hyoid bone when produced by combined geniohyoid muscle stimulation or combined geniohyoid and mylohyoid or combined geniohyoid and thyrohyoid muscle stimulation and change in UES pressure coincident with stimulation. Pearson correlation coefficients from the data depicted here demonstrated a correlation of r=−0.616 with a p value of 0.025. The correlations between pressure change and movement were non-significant when combinations of the mylohyoid and combinations for the thyrohyoid muscles were determined. The results shown in Example 3 demonstrate a desirable embodiment wherein combined muscle stimulations involving the geniohyoid muscle produces anterior motion in the hyoid bone comparable to what happens during swallowing. Furthermore, this motion can produce a drop in UES pressure.

Figure 7:
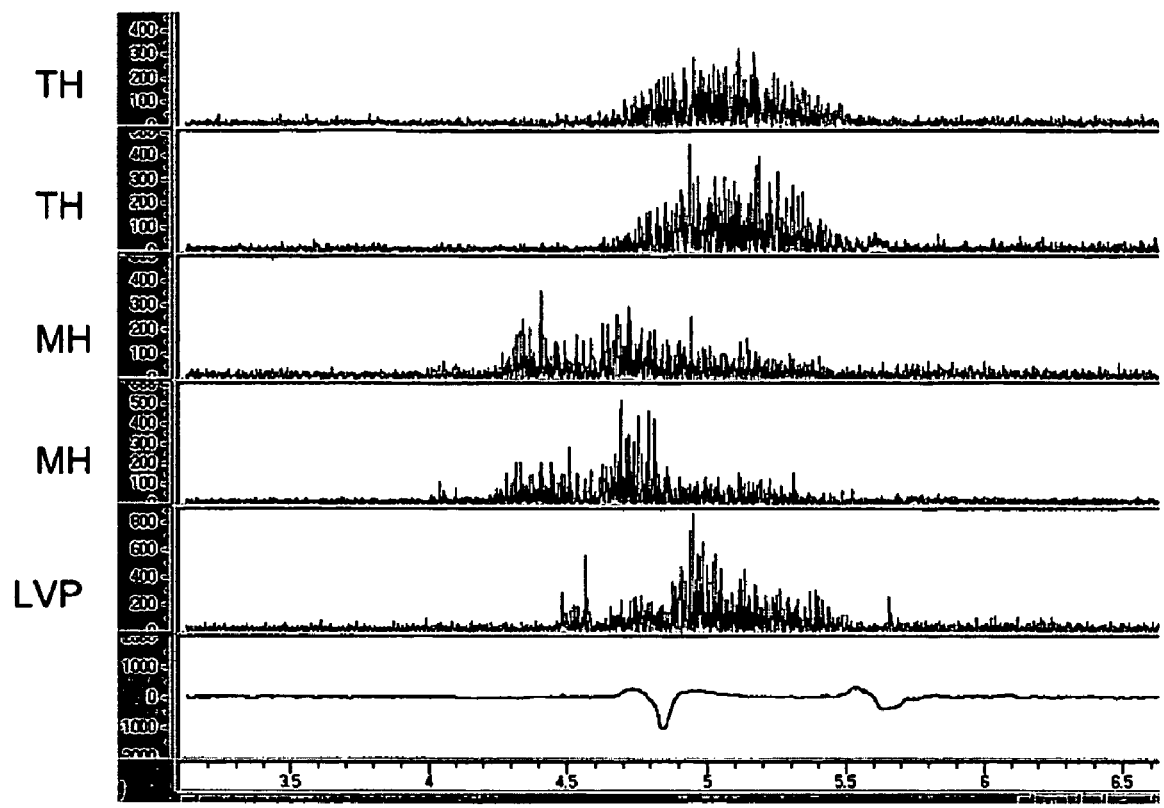

According to yet another embodiment, subjects with implanted electrodes quickly learn to coordinate button pressing with the onset of pharyngeal swallowing. This is important for medical use of muscle stimulation because dysphagia often stems from central nervous system injury, leaving peripheral muscles intact and functional but without appropriate central nervous system control. In patients with chronically impaired laryngeal elevation, movement extent or timing can now be activated through functional electrical neuromuscular stimulation (FES), timed to onset at the beginning of the pharyngeal phase of swallowing thus improving airway protection and swallowing safety. Example 4 shows muscle activation timing that corresponds with this result. As seen in FIG. 7, the usual pattern of muscle activation during the pharyngeal phase of swallowing is activation in the mylohyoid followed by the thyrohyoid. The onset and offset of laryngeal movement for swallowing is indicated by the piezoelectric movement tracing in the lowest panel of this figure.

Figure 8:
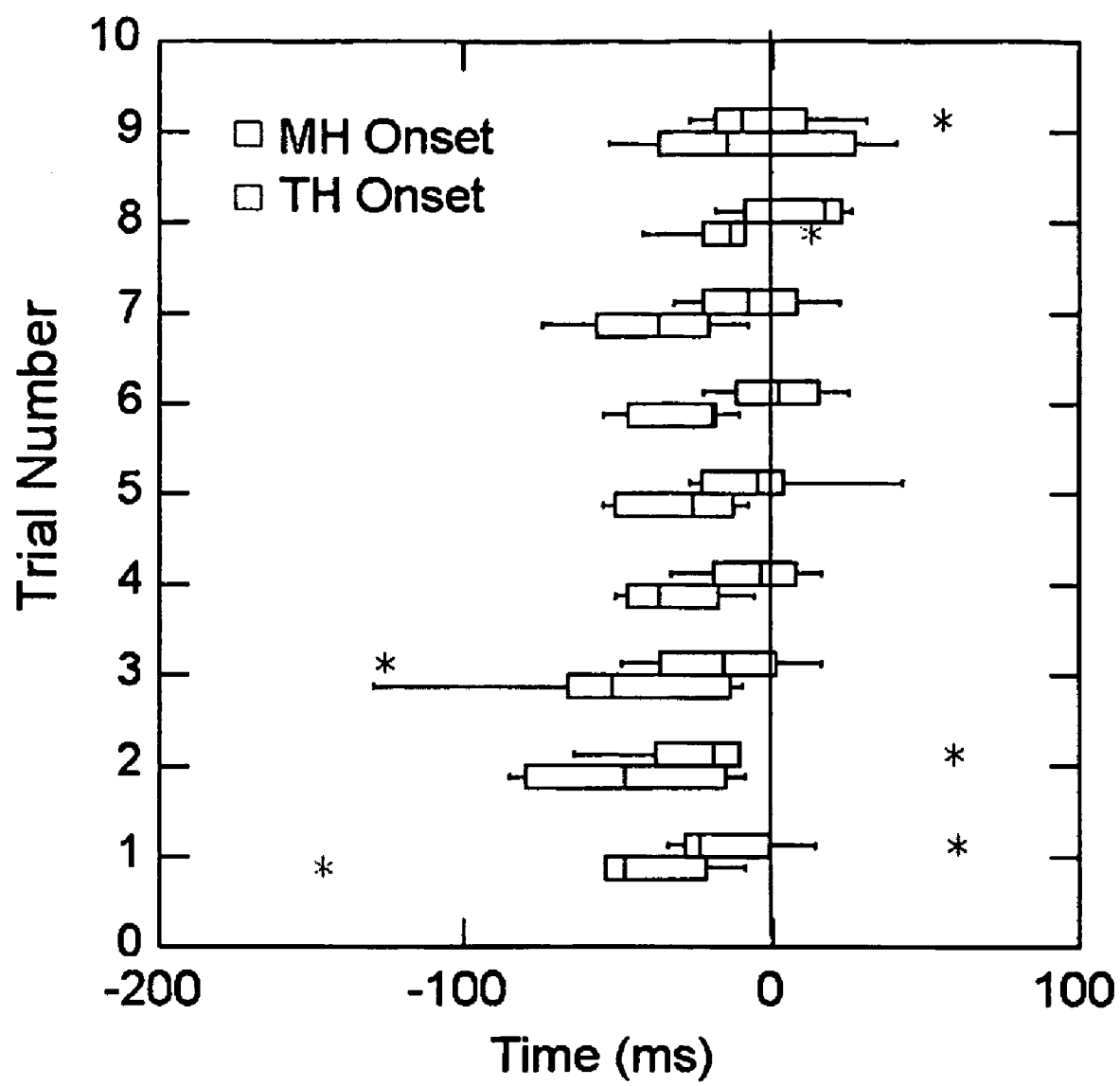

As summarized in FIG. 8, stimulation onset time is at 0. In the first trial, stimulation onset was delayed, occurring an average of 50 milliseconds following the median of the onset time of the mylohyoid muscle activation and about 20 ms after onset of the thyrohyoid. By the $4^{th}$ trial the time of onset of the thyrohyoid and button press stimulation was coincident, with no delay. This occurred spontaneously without instruction, indicating that subjects could improve quickly in their ability to trigger stimulation at the same time as an intended swallow. The results from Example 4 indicate that normal persons can easily and spontaneously coordinate the onset of a button press with the onset of muscle activation for the pharyngeal component of swallowing. Accordingly, patients with dysphagia can learn to coordinate a button press with swallowing onset. In other embodiments, other muscle movements similarly are quickly learned in a similar manner.

Figure 10:
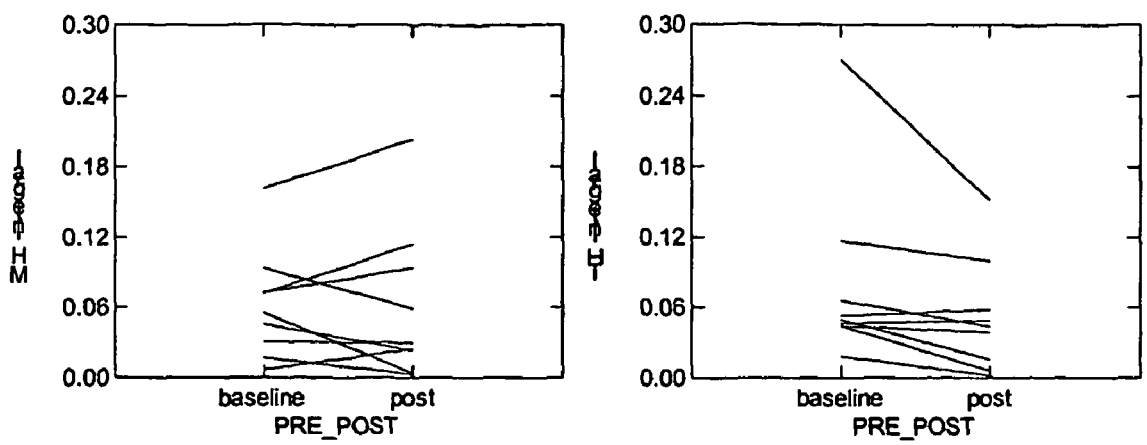
Figure 11:
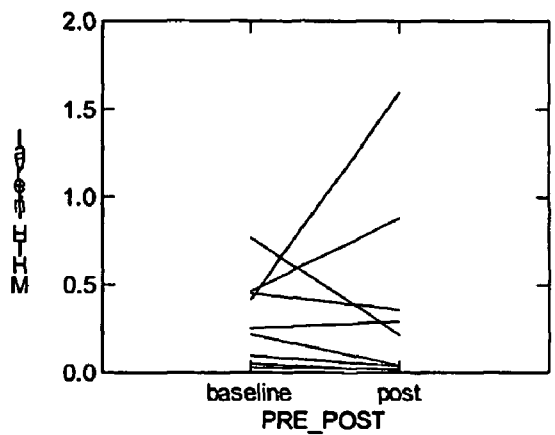

In another embodiment, muscle stimulation as described herein augments a patient's residual movement that occurs during a volitional muscle activity, such as swallowing. As seen in the results of Example 5, subjects did not adapt their muscle activation levels, duration and timing following stimulation trials. See FIGS. 9 and 10, which show the duration of muscle activation prior to and following stimulation. FIG. 11 further shows that timing of mylohyoid onset with respect to thyrohyoid onset did not change during a 10 trial adaptation period.

Because the speed of movement with stimulation approximated that of a swallow, these data show that neuromuscular stimulation can initiate earlier movement onset in patients whose laryngeal elevation is delayed. It was also demonstrated that outside switch controlled sustained stimulation with the participant at rest can produce a stable period of maximum effect that can be measured accurately. During swallowing attempts, a volitional, patient-operated switch can thus provide laryngeal elevation at an appropriate time. In other embodiments the switch actuator that is controlled by the user is adapted to respond to physical movements suited to a patient's weakened or altered condition. For example, the device may be on an eating implement (a spoon), a foot switch, a head movement switch, an arm switch, a finger switch, a torso movement switch, a double simultaneous eye blink switch, an eyebrow movement switch, or a hand switch.

Although a switch mechanism generally is a commonly used external device in embodiments of the invention, other devices advantageously may be employed as will be appreciated by a skilled artisan both for switching and also other aids to performance. For example, the external device may communicate with the signal generator by radio frequency or electromagnetic signals that penetrate the body, using for example, radio waves or light waves. The external device may communicate by other methods, such as ultrasonic vibrations or magnetic fields. The signal generator responds by altering its program and/or using energy to drive the electrode(s). The energy used may be replenished from outside as well. For example, a magnetic coupling device as is known in the art may add electrical energy to a storage reservoir of the implant (ex. a capacitor or rechargeable battery).

The communication between the implanted signal generator and the outside can be used in multiple ways. In an embodiment, an outside controller preferably is used to set parameters of the electric signals produced by the stimulus generator to stimulate muscle via the implanted electrodes, based on observations from outside the body. For example, the effects of different pulse types on stimulating muscles involved in swallowing may be monitored by a digital camera, as exemplified in Example 1. Another related and accurate method for obtaining feedback via videofluoroscopy is shown in Logemann (2002). Other feedback detection systems are used in embodiments of the invention. For example, a piezo electric device may be strapped to the body and signals produced from the crystal used to indicate the timing of muscle movement onset and offset. A comparison between the detected signal(s) and pulses to the intramuscular stimulators may be carried out by routine analysis to determine optimum or improved pulse types. Such calibration normally is carried out after initial implantation of electrodes but also may be carried out in brief form, or in a comprehensive form at later time periods to compensate for changes in muscle and electrode performance. The stimulus response data obtained by systems as described herein also may be used to monitor progression of muscle health. For example, improved muscle response to a standard calibration pulse can indicate improved muscle bulk or conditioning.

Stimulatory and feedback/calibration systems for speech and voice embodiments of the invention may be implemented in similar ways. Sound detectors preferably are used for many of these latter embodiments. For example, the amplitude, frequency control and the like of elicited vocal or speech sounds may be matched to electrode driving pulses to determine optimum pulses for initiating, complementing, or augmenting normal speech and vocalization. The sound detectors may include contact microphones placed on the skin to sense vocal cord vibration through the skin or sonic vibrations of air may be detected by a microphone. Other detectors and methods of their use are readily appreciated by skilled artisans.

Each document cited herein is specifically incorporated in its entirety by reference. The following examples are presented by way of illustration and not by way of limitation.

EXAMPLE 1

This example demonstrates intra-muscular stimulation of swallowing and is also detailed in *J. Applied Physiology*, 94: 128-134, (2003), which is incorporated by reference in its entirety, particularly with respect to methodological details relevant to the present examples.

Fifteen healthy men, each selected for his highly visible thyroid prominence, participated in this study. Average age was 42 years (range 28 to 62). Normal laryngeal structure and function was confirmed on fiberoptic laryngeal examination by an otolaryngologist (E. M.). A lateral view of the neck surface was video recorded during each trial for data analysis. To aid later video data analysis, a 5 cm×3 mm strip of white tape was adhered to the left side of the participant's neck parallel to the direction of movement of the thyroid prominence during swallowing. Placement of the tape was sufficiently lateral to assure that the underlying skin did not move in conjunction with the prominence during swallowing.

Local subcutaneous 0.1 ml injections of 2% lidocaine HCl solution were used to anesthetize the skin prior to the insertion of needle electrodes into the muscles. Neuromuscular stimulation was delivered with a Nicolet Viking IV system (Madison, Wis.) using two independently controlled bipolar electrical stimulators. Optimal electrode position and depth were estimated using anatomical landmarks, and tested by neuromuscular stimulation (0.5-4.0 mA, 200 μs biphasic pulses at 30 Hz lasting 1-2 s) with a monopolar stimulating needle electrode paired to a surface reference electrode adhered to the participant's neck or arm.

For a given implanted muscle, once the desired physiological action was produced, the monopolar needle was withdrawn and a 0.002" diameter hooked wire electrode inserted in its place via a 27-gauge needle. The tip of the hooked wire electrode was bared of insulation for 1-2 mm, and both the needle and electrode wire were gas sterilized prior to use. Placement of the hooked wire electrode was confirmed using the previously described criteria, and if satisfactory, stimulation amplitude was gradually increased from 0.5 mA to a level that achieved marked movement without report of discomfort by the participant, usually between 3 and 6 mA. The maximum stimulation amplitude delivered to any site was 7 mA.

Video recordings were made using a Panasonic KS152 video camera positioned on a tripod approximately 0.8 m on the left and level with the participant, providing a lateral view of the entire neck and jaw region. For display purposes, a time stamp (Horita TRG-50PC) was mixed with the video signal. A grid of 6 mm squares was placed approximately 10 cm to the right of the participant's neck during each trial to facilitate observation of prominence movement.

Trials were videotaped during stimulation of each mylohyoid, thyrohyoid, and geniohyoid muscle, during synchronous stimulation of an ipsilateral mylohyoid and thyrohyoid muscle pair, during bilateral mylohyoid stimulation, and during bilateral thyrohyoid muscle stimulation. In addition, reference recordings were made of each participant while swallowing 2 ml of water. Video recordings were obtained from each stimulation site and digitally captured. Digitization was carried out with a personal computer equipped with a video capture board at 60 fields/second with a frame size of 608× 456 pixels.

Each video sequence began while the participant was at rest, approximately 1 second prior to the onset of stimulation or swallow, and ended after the cessation of movement and a return to rest. Motus 2000 software (Peak Performance Technologies Inc., Englewood Colo.) was used to extract kinematic measures from the digitized video. Using a cursor, points were manually placed onto each video frame to mark the peak of the thyroid prominence, as well as 2 points along a rostral-caudal line approximating the postural angle of the participant, guided by a strip of white tape adhered to the side of the neck. Thus, during data acquisition vertical movement was on the Y-axis coordinate frame parallel to the participant's postural angle. Measures were converted from pixels to millimeters for each recording using either the grid or the measured strip of tape as a calibration marker, with one method applied for each participant. Kinematic data were then smoothed using a low-pass Butterworth filter with a cutoff frequency of 3 Hz, and exported to a spreadsheet for graphing and statistical analysis.

The amount of elevation achieved on a swallow was the difference in millimeters between the thyroid position at rest and the peak value, computed as the mean of 3 data points immediately before and 3 points after the peak (7 data points over 100 ms). Elevation on stimulation was the difference in millimeters between the position of the thyroid prominence at rest and its position during a 500 ms period of stimulation when the thyroid position was most steady. Thyroid prominence velocity was calculated as the peak of the $1^{st}$ derivative of its position. To normalize the data, all stimulation measures for each participant were converted to a percentage of the movement or velocity achieved during that participant's 2 ml water swallow (% swallow elevation or % swallow velocity).

Measures of thyroid prominence movement during 2 ml water swallows by the 15 participants averaged 17.56 mm (±4.17), with an average velocity of 72.67 mm/s (±29.98). The mean intra-rater difference was 0.59 mm for examiner 1, and 0.70 mm for examiner 2 (t=0.47). The mean inter-rater difference between measures was 1.59 mm. The mean percent measurement error, therefore, was 3.67% within examiners and 9.05% between examiners on measures of swallow. The mean difference between examiners was 1.2% swallow elevation (SD=6.58%). Measures obtained by the two examiners were not significantly different (t=0.67, p=0.52).

In single site stimulation tests, stimulation was conducted in 28 mylohyoid sites and 30 thyrohyoid sites across the 15 participants. Geniohyoid stimulation was performed in 12 sites in 9 participants. Despite the distinct criteria used to define electrode placement in the mylohyoid, thyrohyoid, and geniohyoid muscles, individual stimulation of those muscles did not produce significantly different thyroid prominence elevation or velocity (Wilks' Lambda=0.965; F=0.599; df=4, 134; p=0.664). Mean laryngeal elevation for these 3 muscles during stimulation was 5.08 mm (±3.81), or 28.30% (±19.76%) of the elevation produced by the same participants during a 2 ml of water swallow. Mean movement velocity for the 3 muscles was 31.25 mm/s (±15.53), or 49.69% (±31.29%) of the velocity produced during a swallow.

Single vs. paired site stimulation tests also were carried out. Bilateral mylohyoid stimulation was recorded in 12 participants, bilateral thyrohyoid was recorded in 9, and combined ipsilateral mylohyoid and thyrohyoid stimulation was recorded in 11 participants. Repeated ANOVAs compared paired stimulation with single muscle stimulation only in those participants who had received both. For example, the mean of right and left single thyrohyoid stimulation was compared to bilateral thyrohyoid stimulation, and the mean of right mylohyoid and right thyrohyoid single muscle stimulation was compared to paired ipsilateral stimulation of those same muscles. A significant within-subjects effect was found for elevation (F=24.96, df=1, p<0.0001), indicating that paired stimulation yielded greater laryngeal elevation than single muscle stimulation for the 3 muscle pairings (right and left mylohyoid; right and left thyrohyoid; and ipsilateral thyrohyoid and mylohyoid). Mean elevation achieved by paired stimulation was 8.90 mm (±5.50), or 49.07% (±27.49) of swallow elevation, compared to 5.52 mm (±3.22) or 30.14% (±17.52) achieved by stimulation of those same muscles individually. Despite these group effects, no effect of muscle, between subjects, was found for elevation (F=0.51, df=2, p=0.608). Thus, the bilateral mylohyoid, bilateral thyrohyoid, and ipsilateral mylohyoid and thyrohyoid stimulation results did not differ.

Movement velocity was also significantly greater when produced by paired muscle stimulation than by single stimulation of those same muscles (F=26.23, df=1, p<0.0001). During paired stimulation, laryngeal movement velocity averaged 51.94 mm/s (±23.22) or 82.08% (±43.86) of swallow movement velocity. Those same thyrohyoid and mylohyoid muscles stimulated one at a time produced an average movement velocity of 33.39 mm/s (±11.86) or 54.92% (±31.79). No significant muscle effect was found (F=1.54, df=2, p=0.231). Thus, no muscle pair studied produced faster thyroid prominence movement when stimulated than any other.

EXAMPLE 2

Unless otherwise described, the procedures described above for Example 1 were used for this example, which demonstrates that combined muscle stimulation can move the hyoid bone in the anterior and superior direction and the larynx in the superior direction to the same or a greater extent than occurs during normal swallowing.

The skin at each electrode insertion site was anesthetized with injections of 2% lidocaine. For each site, after numbness was reported, a 27 gauge monopolar needle was inserted in a desired muscle region and a train of stimulating pulses (200 µs width, 0.5-5.0 mA amplitude, 30 Hz frequency) was delivered to induce muscle contraction. Needle location was found to be mylohyoid (MH) if the stimulated contraction retracted the submental tissue and moved the thyroid prominence superiorly. A thyrohyoid (TH) location was found if the thyroid prominence moved superiorly and twisted contralaterally. Once a desired insertion site was located, the locating needle was removed and a 0.002" monopolar hooked wire electrode was inserted in its place using another 27 gauge needle as a carrier. Geniohyoid (GH) was said to be stimulated if the submental tissue became bulked and the hyoid moved anteriorly. Electrode placement accuracy was confirmed using the same criteria described above. Stimulation amplitude gradually was increased to the highest level comfortably tolerated (maximum ≦6 mA).

A videofluoroscopic study of laryngeal elevation study was carried out with six normal volunteers between 35 and 65 years of age that lacked neurological, otolaryngological, psychiatric, swallowing and speech and hearing problems as determined by medical history and examination by a physician. Muscle movements from stimulation were compared with that from normal swallowings of thin and thick liquids and paste. Six stimulation trials were carried out with different muscle combinations as follows: bilateral mylohyoid; bilateral geniohyoid; bilateral thyrohyoid; ipsilateral mylohyoid and geniohyoid; ipsilateral mylohyoid and thyrohyoid; and ipsilateral geniohyoid and thyrohyoid. Unstimulated swallows included 5 ml bolus of thin liquid and 10 ml bolus of pudding barium material. Combined button press stimulation, swallow and sham stimulation were included as trials. Measurements compared both speed and extent of movements on the x (anterior-posterior) and y (superior-inferior) axes.

For measurements of laryngeal and hyoid movements a reference coin was taped to the side of a subject's neck. Distance of the hyoid and arytenoids was measured on 2 planes from the postural line along C4 of the cervical spine in millimeters as shown in FIG. 1. This figure shows, (see arrows), measurement points (as small round circles) on the hyoid and cartilage in x-y space relative to the postural line and the x direction measure form the top of the subglottal air column.

Within the anterior-posterior plane, a horizontal line along the surface of the C4 vertebra serves as an origin for superior-inferior measurements. The superior-inferior plane is defined by a line along the anterior surface of the C4 vertebra. This line is a 0 reference for the anterior-posterior plane. The intersection of the two lines occurs at the anterior superior point of C4 and defines 0 for both planes, as seen in FIG. 1. The images are analyzed by Peak Performance Image Processing software for kinematic analysis. By marking the 2 points in x and y space, the software computess the displacement over time and the velocities of the trajectories during the stimulations and during normal swallows.

Data from six individuals are summarized in FIGS. 2-4. Three measurements relative to the cervical vertebra are shown in these figures. The histograms depicted in these figures show means of 5 subjects during sham stimulation. The label biMH means bilateral mylohyoid, BiTH means bilateral thyrohyoid, BiGH means bilateral geniohyoid, MHTH means simultaneous stimulation of the mylohyoid and thyrohyoid on one side, MHGH means simultaneous stimulation of the mylohyoid and geniohyoid on one side, and GHTH means simultaneous stimulation of the geniohyoid and thyrohyoid on one side. FIG. 2 displays data from anterior hyoid movement, FIG. 3 shows hyoid elevation results, and FIG. 4 depicts laryngeal elevation data, based on the position of the tip of the subglottic air column. Data were normalized for inter-individual variation by computing the 3 measurements as percentages of movements that occur within the same subject while swallowing 5 ml of liquid.

EXAMPLE 3

Unless otherwise described, the procedures described above for Example 1 were used for this example, which quantitatively demonstrates decreased pressure in the upper esophageal sphincter in response to anterior motion of the hyoid induced by combined muscle stimulation.

To record changes in pressure exerted at the upper esophageal sphincter, a manometer was inserted into the upper esophagus. The height was adjusted until the point of maximum resting pressure was identified and recorded with the transducer. The transducer pressure signal was examined before each stimulation or swallow to determine if the transducer had returned to the same position.

Simultaneous measurements of upper esophageal sphincter pressure both during stimulation at rest and without stimulation during normal swallowing determined whether the decrease in pressure, representing opening of the upper esophageal sphincter (UES) during mylohyoid stimulation, relates to the degree and/or duration of laryngeal elevation during neuromuscular stimulation.

The peak negative manometric pressure readings and the intervals of negative manometric pressure were measured during a) 6 stimulation trials at rest, and b) regular swallows of 5 ml of thin liquid and 10 ml of pudding of barium paste. Pressure calibration signals were digitized for linear interpolation into mmHg.

Figure 5:
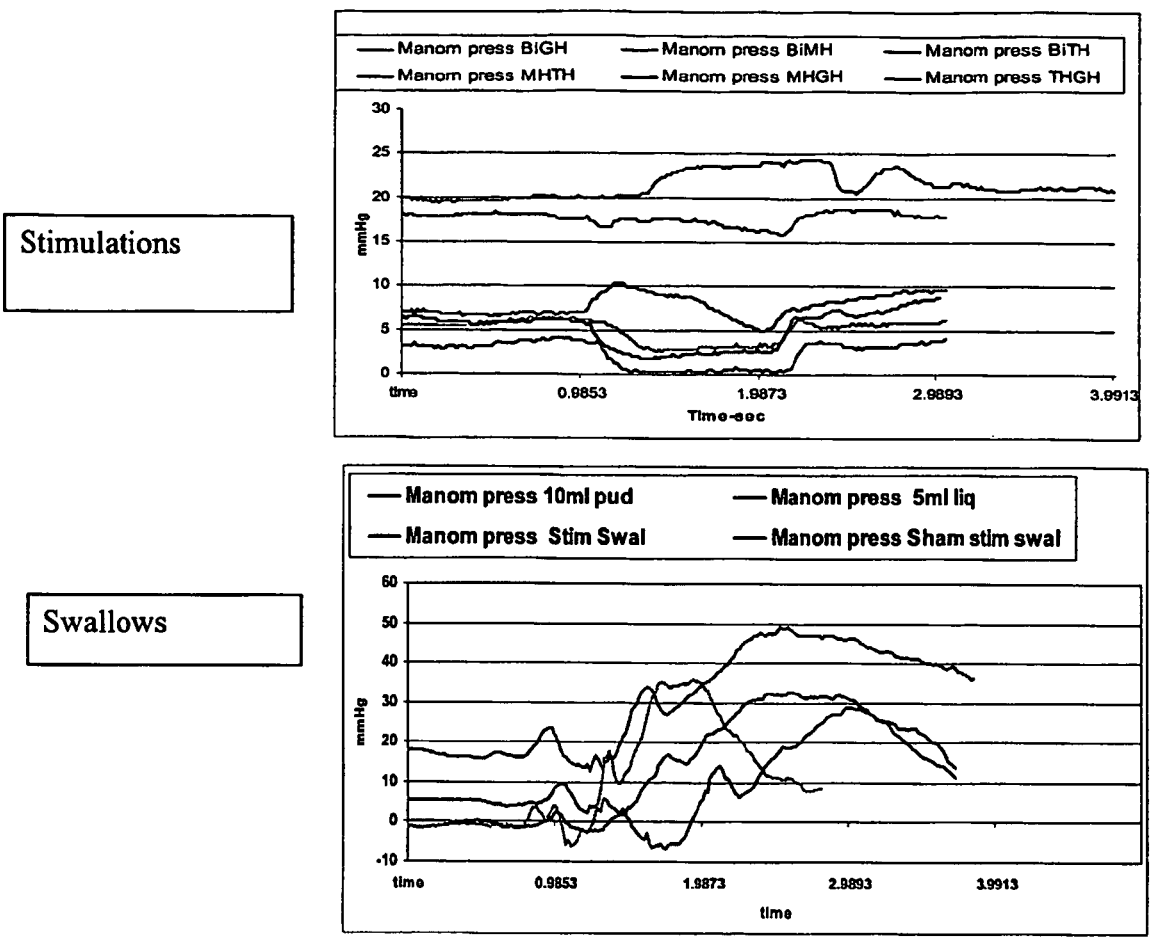

FIG. 5 shows manometry tracings of pressure changes during combined muscle stimulations (top box) and during swallows of various bolus size and consistencies (bottom box).

EXAMPLE 4

Unless otherwise described, the procedures described above for Example 1 were used for this example, which demonstrates that subjects can learn to coordinate button pressing with the onset of the pharyngeal swallowing within a few trials spontaneously without instruction.

Mylohyoid and thyrohyoid EMG activity were recorded during 3 baseline swallows of 2 ml water in 9 healthy adult volunteers. Then an adaptation paradigm was carried out in which each volunteer repeatedly swallowed while triggering neuromuscular stimulation of one mylohyoid and thyrohyoid muscle pair. The data were analyzed to examine the degree of correspondence between the onset of muscle activation for swallowing and the time when subject started the stimulation trigger. This correspondence was examined over 9 trials wherein subjects were instructed to press the button at the same time as they began swallowing. FIGS. 6 and 7 show representative muscle activation activities and onset time comparisons, respectively.

EXAMPLE 5

Figure 9:
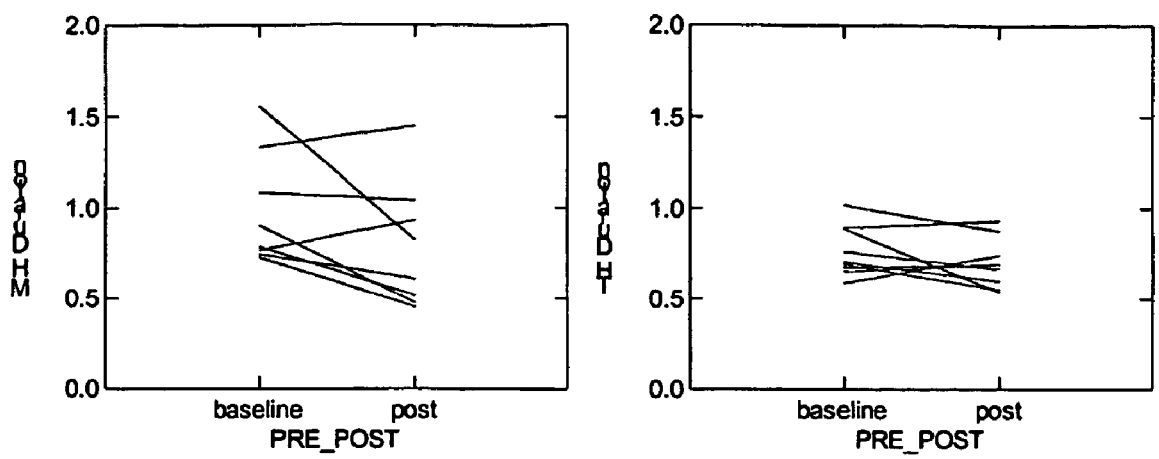

Unless otherwise described, the procedures described above for Example 1 were used for this example, which demonstrates that the effects of muscle stimulation are additive in that subjects do not reduce the amplitude or the duration of their muscle activity with stimulation. As described for Example 4, the effects of stimulation on muscle activation for swallowing was also examined in nine subjects. In this example, a subject coordinating his or her stimulation with their own swallowing for ten trials. In a subsequent trial, the stimulation was unexpectedly withdrawn. This is termed a "stimulation foil" wherein volunteers anticipate stimulation but do not receive stimulation. This method allowed examination of how subjects might have altered muscle activity to adapt to stimulation by comparing the pre stimulation baseline muscle duration and integrated activity with that during foil stimulation. As shown in FIG. 8, the duration of mylohyoid muscle activity and thyrohyoid activity did not change after stimulation ($F=0.158$, $p=0.696$). This result did not differ among muscles studied ($F=0.045$, $p=0.828$). Similarly as shown in FIG. 9 the integrated activity of the mylohyoid muscle and the thyrohyoid did not change after stimulation ($F=2.643$, $p=0.124$) and this did not differ by muscle ($F=2.551$, $p=0.130$). Data also were obtained that show (FIG. 10) that that the interval between mylohyoid onset and thyrohyoid onset did not change after 10 stimulation trials ($F=0.243$, $p=0.636$).

Of course, changes and modifications to the embodiments presented herein are readily understood by the skilled artisan after reading this specification and furthermore, such changes and modifications may be practiced within the scope of the appended claims.

What is claimed is:

1. A method of coordinate control of movements in the upper airway during swallowing in a subject, comprising:
   a) implanting at least two different intramuscular stimulators into a thyrohyoid muscle and at least one other hyoid muscle involved in the upper airway and vocal tract of the subject,
   b) implanting signal generator in the subject that generates electrical pulses to the at least two intra-muscular stimulators at a frequency of about 10 to 75 Hz;
   wherein electrical pulses from the signal generator activate the at least two different muscles to produce the coordinate movement control during swallowing.

2. The method of claim 1, wherein at least two different muscles are chronically implanted and the coordinate control comprises enhancing a portion of the complex pattern of movements, or producing a portion of the complex pattern of movements.

3. The method of claim 1, wherein the at least one hyoid muscle is selected from the group consisting of at least one mylohyoid muscle, one hyoglossus, at least one geniohyoid muscle, and combinations thereof.

4. The method of claim 1, wherein the signal generator generates electrical pulses to the at least two intramuscular stimulators in a manner suitable for initiating movements in a subject delayed in initiating movement during swallowing.

5. The method of claim 1, wherein the signal generator generates electrical pulses to the at least two intramuscular stimulators in a manner suitable for augmenting movement in a subject with limited range and speed of movement during swallowing.

6. The method of claim 1, wherein the at least muscles protect the airway during food ingestion.

7. The method of claim 1, wherein the muscles protect the airway during food ingestion by raising the hyo-larynx to reduce the entry to the vestibule.

8. The method of claim 1, wherein the two muscles raise the hyp-larynx and/or open the upper esophageal sphincter.

9. The method of claim 1, further comprising a switch located outside the subject's body and operable by the subject, wherein the switch activates the implanted signal generator to control either the onset and/or offset of stimulation of the at least two implanted stimulators.

10. The method of claim 1, further comprising a switch located outside the subject's body and operable by the subject, wherein the switch activates the implanted signal generator to control intramuscular stimulation to prevent aspiration during swallowing.

11. A method of moving the hyoid bone, and/or parts of the upper airway within an animal by two or more different controlled muscles, comprising:
    a) implanting at least one electrode into each of two or more different muscles, wherein one of the muscles is the thyrohyoid and the other muscle of the two or more different muscles is a hyoid muscle;
    b) electrically connecting each electrode to an indwelling subcutaneous signal generator capable of generating a pattern of stimulation; and
    c) energizing the controlled muscles at the same time with a signal of about 10 to 75 Hz by the signal generator to synergistically move the parts of the upper airway, or hyoid bone.

12. The method of claim 11, wherein the animal is a human and step c) is carried out by operating a switch under conscious control of the human.

13. The method of claim 11, wherein the hyoid muscle is selected from the group consisting of the mylohyoid muscles, the hyoglossus, the geniohyoid muscles, and combinations thereof.

14. The method of claim 11, wherein the hyoid bone is moved by simultaneous stimulation of at least one mylohyoid muscle, hyoglossus and at least one geniohyoid muscle.

15. A method of simultaneously moving the hyoid bone and larynx and opening the upper esophageal sphincter within an human via at least one muscle attached to the hyoid bone, comprising:
    implanting at least one electrode into each of two or more said muscles;
    electrically connecting each electrode to a signal generator capable of generating a complex pattern to activate the muscle attached to the electrode; and
    energizing electrodes in at least two of the muscles at the same time at a frequency of 10 to 75 Hz with the signal generator, thereby synergistically moving the hyoid bone and/or opening the upper esophageal sphincter.

16. The method of claim 15, wherein one or more of the electrodes are Peterson-like electrodes.

17. A method of compensating for variations in electrode placement when stimulating two or more muscles to effect a coordinated bone, sphincter, structure, tissue or cartilage movement in the hypopharynx, or upper airway movement, comprising:
    a) implanting a first electrode in a thyrohyoid muscle;
    b) implanting a second electrode in at least one hyoid muscle;
    c) stimulating the first electrode and determining the effect of stimulation on movement of the bone, sphincter, tissue, structure or cartilage;
    d) stimulating the second electrode implanted in the tissue and determining the effect of stimulation on movement of the bone, sphincter, tissue, structure or cartilage; and comparing the effects from c) and d) to determine an optimum coordination of signals to the first and second electrodes to obtain a desired direction and strength of the bone, sphincter, tissue, structure or cartilage movement.

18. The method of claim 17, wherein the strength and timing of the electrical signal to at least one of the electrodes implanted in the tissue is altered to compensate for the effect of electrode placement on the induced movement.

19. A system for coordinating the onset and offset of two or more different electrical signals to electrodes implanted in tissue used to coordinately control a bone, sphincter, tissue, structure or cartilage movement in the hypopharynx, or upper airway to protect the airway, the system comprising:
    a controller with a stored program that directs a signal generator to send electrical pulses to each of at least two electrodes in a determined pattern, wherein the determined pattern of electrical pulses coordinates the onset and offset of two or more different electrical signals to the at least two electrodes to protect the airway, each signal sent to a different electrode implanted in the tissue,
    the implantable signal generator comprising a processor, wherein the processor is configured to deliver an electrical signal to each of the electrodes at overlapping time periods that are selected to induce muscle contractions in the different muscles at overlapping or identical times,
    at least two intramuscular electrodes suitable for implantation in a muscle in the hypopharynx, or upper airway,
    a switch located external to the body and configured to be activated by a human, wherein the switch is configured to communicate to the signal generator upon activation by the human, and
    a sensor device;
    wherein the controller under the direction of the stored program directs the signal generator to coordinate the onset and offset of two or more different electrical signals to activate each of the intra-muscular electrodes to move the bone, sphincter, tissue, structure or cartilage to protect the airway.

20. The system of claim 19, wherein one signal generator is used to control all electrodes, and the sensor device is configured to measure the movement of a body part.

21. The system of claim 19, wherein movement of either the hyoid bone, the thyroid prominence, the larynx, the upper esophageal sphincter, upper airway or vocal tract are transduced.

22. A system for moving a cartilage within a subject comprising:
    an implantable signal generator comprising a power source and a processor;
    a first electrode implantable in a first hyo-laryngeal muscle attached to the cartilage and operably connected to the signal generator;
    a second electrode implantable in a second different hyo-laryngeal muscle attached to the same cartilage and operably connected to the signal generator; and a switch located external to the body and configured to be activated by the subject, wherein the switch is configured to communicate to the signal generator upon activation by the subject;

wherein the processor is configured to generate a signal of about 10 to 75 Hz to each of the first and second electrodes at the same time and to effect a swallow elevation and laryngeal movement velocity in the cartilage that exceeds swallow elevation and laryngeal movement velocity made by pulses sent to the muscles at separate times.

23. The system of claim 22, wherein the cartilage is a laryngeal cartilage.

24. The system of claim 22, wherein the cartilage is the thyroid cartilage.

25. A system for control of stimulation during swallowing of a human with dysphagia comprising:

at least two intra-muscular electrodes;

an implantable signal generator connected to the at least two electrodes and that comprises a processor configured to control the output energy to the electrodes according to a determined pattern, a controller with a stored program that directs the signal generator to send electrical pulses to each of the at least two electrodes in the determined pattern, wherein the determined pattern of electrical pulses comprises a frequency of about 10 to 75 Hz and moves at least two different muscles that control hyoid bone movement so that the hyoid bone moves up at least 80% of the elevation of a normal swallow, and;

a power supply that provides energy for the signal generator;

a sensor configured to detect physiological movement; and a switch operable by the human that controls the signal generator, wherein the operation of the switch by the human activates the controller to direct the signal generator to send electrical pulses to each of the at least two electrodes in the determined pattern.

26. The system of claim 25, wherein the intramuscular electrodes are Peterson-like electrodes.

27. The system of claim 25, wherein the signal generator and power supply are provided within the same implant.

28. The system of claim 25, further comprising a weak muscle contraction signal detection circuit comprised of:

an electrode embedded in a muscle used for swallowing;

an electrical lead from the embedded electrode to a signal processor to recognize a detected weak signal indicating a desire to swallow;

a trigger input to the controller from the signal processor upon recognition of the detected signal; and a stored program in the controller that directs the signal generator to output muscle contraction signals through electrodes to the at least two muscles in response to recognition of the detected weak signal.

29. The system of claim 28, wherein the electrode embedded in a muscle used for swallowing also is used for stimulating the muscle.

30. The system of claim 25, wherein at least two different muscles are selected from the group consisting of the intrinsic laryngeal muscle(s), the extrinsic laryngeal muscle(s), the bilateral mylohyoid muscle(s), the bilateral thyrohyoid muscle(s), the bilateral geniohyoid muscle(s), the unilateral mylohyoid muscle(s), the unilateral geniohyoid muscle(s), the unilateral thyrohyoid muscle(s), the unilateral thyroarytenoid muscle(s), and the bilateral thyroarytenoid muscle(s).

31. The system of claim 25, wherein the controller also has a stored program that directs the signal generator to send a reference signal to each of the at least two electrodes embedded in muscle.

32. The system of claim 25, wherein the stored program directs the signal generator to send the signal to each of the at least two electrodes embedded in muscle at overlapping times.

33. The system of claim 32, wherein the stored program directs the signal generator to send the signal to each of the at least two electrodes embedded in muscle at the same time.

34. The system of claim 25, wherein the stored program directs the signal generator to send a signal with a complex wave form.

* * * * *

UNITED STATES PATENT AND TRADEMARK OFFICE
CERTIFICATE OF CORRECTION

| | | |
|---|---|---|
| PATENT NO. | : 7,606,623 B2 | Page 1 of 1 |
| APPLICATION NO. | : 10/529401 | |
| DATED | : October 20, 2009 | |
| INVENTOR(S) | : Ludlow et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this

Fourteenth Day of December, 2010

David J. Kappos
*Director of the United States Patent and Trademark Office*